United States Patent
Lee et al.

(10) Patent No.: US 10,470,744 B2
(45) Date of Patent: Nov. 12, 2019

(54) ULTRASOUND DIAGNOSIS APPARATUS, ULTRASOUND DIAGNOSIS METHOD PERFORMED BY THE ULTRASOUND DIAGNOSIS APPARATUS, AND COMPUTER-READABLE STORAGE MEDIUM HAVING THE ULTRASOUND DIAGNOSIS METHOD RECORDED THEREON

(71) Applicant: SAMSUNG MEDISON CO., LTD., Hongcheon-gun (KR)

(72) Inventors: Kwang-hee Lee, Hongcheon-gun (KR); Sung-yoon Kim, Hongcheon-gun (KR); Gil-ju Jin, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 514 days.

(21) Appl. No.: 14/842,383

(22) Filed: Sep. 1, 2015

(65) Prior Publication Data

US 2016/0058422 A1    Mar. 3, 2016

(30) Foreign Application Priority Data

Sep. 1, 2014    (KR) .................... 10-2014-0115694

(51) Int. Cl.
*A61B 8/08*    (2006.01)
*A61B 8/00*    (2006.01)
(Continued)

(52) U.S. Cl.
CPC .......... *A61B 8/5207* (2013.01); *A61B 8/0858* (2013.01); *A61B 8/0866* (2013.01);
(Continued)

(58) Field of Classification Search
CPC .... A61B 8/5207; A61B 8/0875; A61B 8/5223
See application file for complete search history.

(56) References Cited

U.S. PATENT DOCUMENTS 6,575,907 B1 *  6/2003  Soferman ............ A61B 5/1075
                                                   128/916
8,649,577 B1    2/2014  Arnold et al.
(Continued)

FOREIGN PATENT DOCUMENTS

KR       10-0233074 B1    12/1999
KR    10-2011-0132280 A    12/2011
(Continued)

OTHER PUBLICATIONS

Communication dated Nov. 17, 2015 issued by the Korean Intellectual Property Office in counterpart Korean Patent Application No. 10-2014-0115694.
(Continued)

*Primary Examiner* — Rochelle D Turchen
(74) *Attorney, Agent, or Firm* — Sughrue Mion, PLLC

(57) ABSTRACT

An ultrasound diagnosis apparatus and method capable of efficiently measuring the volume of an object is provided. The ultrasound diagnosis apparatus includes a data acquisition unit configured to acquire ultrasound image data regarding a object including a target bone which is to be diagnosed, and an image processing unit configured to acquire first information about at least one selected from a location of the target bone within an ultrasound image and a length of the target bone, based on volume data included in the ultrasound image data, acquire a boundary surface of a soft tissue that is adjacent to the target bone, based on the first information, and automatically acquire a volume of an interior of the boundary surface of the soft tissue.

27 Claims, 21 Drawing Sheets

(51) Int. Cl.
  *G06T 7/12* (2017.01)
  *G06T 7/62* (2017.01)
(52) U.S. Cl.
  CPC .......... *A61B 8/0875* (2013.01); *A61B 8/4472* (2013.01); *A61B 8/466* (2013.01); *A61B 8/469* (2013.01); *A61B 8/483* (2013.01); *A61B 8/5223* (2013.01); *G06T 7/12* (2017.01); *G06T 7/62* (2017.01); *G06T 2207/10136* (2013.01)

(56) References Cited

U.S. PATENT DOCUMENTS

| | | |
|---|---|---|
| 9,119,591 B2 | 9/2015 | Lee |
| 9,152,854 B2 | 10/2015 | Lee |
| 2011/0066031 A1 | 3/2011 | Lee et al. |
| 2011/0087095 A1 | 4/2011 | Lee |
| 2011/0125016 A1 | 5/2011 | Lazebnik et al. |
| 2011/0196236 A1 | 8/2011 | Swamy et al. |
| 2013/0060121 A1 | 3/2013 | Patwardhan et al. |
| 2013/0272594 A1* | 10/2013 | Zelzer ................ G06T 3/0043 382/131 |
| 2015/0057544 A1* | 2/2015 | Takagi ................ A61B 8/463 600/441 |

FOREIGN PATENT DOCUMENTS

| | | |
|---|---|---|
| KR | 10-1100457 B1 | 12/2011 |
| KR | 10-1121301 B1 | 3/2012 |
| KR | 10-2013-0090740 A | 8/2013 |
| WO | 02/22013 A1 | 3/2002 |
| WO | 03/009762 A1 | 2/2003 |

OTHER PUBLICATIONS

Communication dated Jan. 28, 2016 issued by the European Patent Office in counterpart European Patent Application No. 15183176.5.
Campbell S; "Ultrasonic Measurement of Fetal Abdomen Circumference in the Estimation of Fetal Weight"; An International Journal of Obstetrics; vol. 82; No. 9; Sep. 1975; 1 page total.
Hadlock et al.; "Estimation of Fetal Weight with the Use of Head, Body, and Femur Measurements—A Prospective Study"; American Journal of Obstetrics Gynecology; vol. 151; No. 3; Feb. 1, 1985; 5 pages total.
Schild et al.; "Fetal Weight Estimation by Three-Dimensional Ultrasound"; Ultrasound Obstetrics Gynecology; vol. 16; 2000; 8 pages total.
Vintzileos AM et al.; "Fetal Weight Estimation Formulas with Head, Abdominal, Femur, and Thigh Circumference Measurements"; American Journal of Obstetrics Gynecology; vol. 157; No. 2; Aug. 1987; 1 page total.
Tae-Bok Song et al.; "Fetal Weight Prediction by Thigh Volume Measurement with Three-Dimensional Ultrasonography"; Obstetrics & Gynecology; vol. 96; No. 2; Aug. 2000; 5 pages total.
Wesley Lee et al.; "Birth Weight Prediction by Three-Dimensional Ultrasonography"; Fractional Limb Volume; American Institute of Ultrasound in Medicine; vol. 20; 2001; 10 pages total.
W. Lee et al.; "New Fetal Weight Estimation Models Using Fractional Limb Volume"; Ultrasound Obstetrics Gynecology; vol. 34; 2009; 10 pages total.
Fadi R. Khoury et al.; "Comparison of Estimated Fetal Weights Using Volume and 2-Dimensional Sonography and Their Relationship to Neonatal Markers of Fat"; American Institute of Ultrasound in Medicine; vol. 28; 2009; 7 pages total.
W. Lee et al.; "Prospective Validation of Fetal Weight Estimation Using Fractional Limb Volume"; Ultrasound Obstetrics Gynecology; vol. 41; 2013; 6 pages total.
W. Lee et al.; "Fetal Growth Parameters and Birth Weight: Their Relationship to Neonatal Body Composition"; NIH Public Access—Author Manuscript; Ultrasound Obstetrics Gynecology; vol. 33; No. 4; 2009; 11 pages total.
W. Lee et al.; "Fractional Limb Volume—A Soft Tissue Parameter of Fetal Body Composition: Validation, Technical Considerations and Normal Ranges During Pregnancy"; Ultrasound Obstetrics Gynecology; vol. 33; 2009; 14 pages total.
W. Lee et al.; "Fetal Echocardiography: z-score Reference Ranges for a Large Patient Population"; Ultrasound Obstetrics Gynecology; vol. 35; 2010; 7 pages total.
L. J. Salomon et al.; "Practice Guidelines for Performance of the Routine Mid-Trimester Fetal Ultrasound Scan"; Ultrasound Obstetrics Gynecology; vol. 37; 2011; isuog.org; 11 pages total.
Communication dated Feb. 14, 2018 issued by the European Patent Office in counterpart European Patent Application No. 15183176.5.

* cited by examiner

ULTRASOUND DIAGNOSIS APPARATUS, ULTRASOUND DIAGNOSIS METHOD PERFORMED BY THE ULTRASOUND DIAGNOSIS APPARATUS, AND COMPUTER-READABLE STORAGE MEDIUM HAVING THE ULTRASOUND DIAGNOSIS METHOD RECORDED THEREON

CROSS-REFERENCE TO RELATED PATENT APPLICATION

This application claims the benefit of Korean Patent Application No. 10-2014-0115694, filed on Sep. 1, 2014, in the Korean Intellectual Property Office, the disclosure of which is incorporated herein in its entirety by reference.

BACKGROUND

1. Field

One or more exemplary embodiments relate to an ultrasound diagnosis apparatus, an ultrasound diagnosis method performed by the ultrasound diagnosis apparatus, and a computer-readable storage medium having the ultrasound diagnosis method recorded thereon.

More particularly, one or more exemplary embodiments relate to an ultrasound diagnosis apparatus capable of automatically measuring a physical numerical value of an object during an ultrasound diagnosis, an ultrasound diagnosis method performed by the ultrasound diagnosis apparatus, and a computer-readable storage medium having the ultrasound diagnosis method recorded thereon.

2. Description of the Related Art

Ultrasound diagnosis apparatuses transmit an ultrasound signal generated by a transducer of a probe to an object and receive information regarding an ultrasound echo signal reflected from the object, thereby obtaining an image of a part inside the object. In particular, ultrasound diagnosis apparatuses are used for medical purposes, such as observation of the inside of an object, detection of foreign substances inside the object, and diagnosis of damage thereof. Such ultrasound diagnosis apparatuses have various advantages, including stability, real-time display, and safety because there is no exposure to radiation, compared to X-ray apparatuses, and thus, the ultrasound diagnosis apparatuses are commonly used together with other image diagnosis apparatuses.

Such ultrasound diagnosis apparatuses can be used in fetal biometric measurements. Fetal biometric measurements can be performed to estimate a gestational age of a fetus, evaluate the size of the fetus, and monitor growth of the fetus. Examples of the fetal biometric measurements include volume measurement of a predetermined part of an arm or leg of a fetus. The measured volume may be related to the weight of the fetus. The weight of the fetus can be used as information for use in diagnosing deformity and malnutrition of the fetus. In the related art, it is difficult to estimate the weight of a fetus based on three dimensional (3D) data. In addition, users use different methods to estimate the weight of a fetus based on 3D data. Thus, in the related art, the weight of a fetus is estimated based on two dimensional (2D) ultrasound image data. However, it has been recently reported that estimating the weight of a fetus based on 3D ultrasound image data is more accurate. Moreover, the weight of a fetus may be estimated by measuring the volume of an object of the fetus based on 3D ultrasound image data.

Thus, ultrasound diagnosis apparatuses and methods capable of efficiently measuring the volume of an object are required.

SUMMARY

One or more exemplary embodiments include an ultrasound diagnosis apparatus and method capable of efficiently measuring the volume of an object.

Additional aspects will be set forth in part in the description which follows and, in part, will be apparent from the description, or may be learned by practice of the presented embodiments.

According to one or more embodiments of the present invention, an ultrasound diagnosis apparatus includes a data acquisition unit configured to acquire ultrasound image data regarding a object including a target bone which is to be diagnosed; and an image processing unit configured to acquire first information about at least one selected from a location of the target bone within an ultrasound image and a length of the target bone, based on volume data included in the ultrasound image data, acquire a boundary surface of a soft tissue that is adjacent to the target bone, based on the first information, and automatically acquire a volume of an interior of the boundary surface of the soft tissue.

The image processing unit may three-dimensionally render at least one selected from the target bone and the boundary surface of the soft tissue, based on the volume data.

The ultrasound diagnosis apparatus may further include a display unit configured to display the ultrasound image that is generated by the image processing unit.

The display unit may display at least one selected from the ultrasound image that is based on a 3D-rendered target bone, a boundary surface of a 3D-rendered soft tissue, a cross section of the 3D-rendered target bone, a cross section of the boundary surface of the 3D-rendered soft tissue, and volume data; a length value of the target bone; and a volume value of the interior of the boundary surface of the soft tissue.

The display unit may display an ultrasound image on which the target bone and the soft tissue are distinguished from each other.

The display unit may display at least one selected from a 3D-rendered target bone, a boundary surface of the 3D-rendered soft tissue, a cross section of the 3D-rendered target bone, and a cross section of the boundary surface of the 3D-rendered soft tissue, with different patterns, different colors, and different degrees of transparency.

The image processing unit may acquire a boundary surface of the soft tissue that surrounds at least a predetermined portion of the target bone.

The image processing unit may acquire the boundary surface of the soft tissue such that a ratio of the length of the target bone to a length of the boundary surface of the soft tissue has a predetermined ratio in a lengthwise direction of the target bone.

The predetermined ratio may include at least one selected from a pre-determined ratio and a ratio received from a user.

The image processing unit may acquire the boundary surface of the soft tissue by using at least one selected from an active contour algorithm, segmentation using a cylindrical coordinate system transform, and slice-based segmentation.

By using the active contour algorithm, the image processing unit may extend a predetermined boundary surface from the target bone to the boundary surface of the soft tissue on the ultrasound image, acquire an extension parameter enabling the predetermined boundary surface to extend to the boundary surface of the soft tissue on the ultrasound image, a suppression parameter having an opposite sign to the extension parameter and preventing the predetermined boundary surface from exceeding the boundary surface of the soft tissue on the ultrasound image, and a smoothness parameter of which an absolute value decreases with a decrease in a change rate of an inclination of the predetermined boundary surface at a predetermined point, and acquire the boundary surface of the soft tissue, based on a predetermined function including the extension parameter, the suppression parameter, and the smoothness parameter.

Via the segmentation using the cylindrical coordinate system transform, the image processing unit may transform the ultrasound image to a cylindrical coordinate system, extend a predetermined boundary surface from the target bone to the boundary surface of the soft tissue on the ultrasound image, acquire a variation parameter of which an absolute value decreases with an increase in a luminance change rate of a voxel in an ultrasound image obtained by the transformation to the cylindrical coordinate system, and a smoothness parameter of which an absolute value decreases with a decrease in a change rate of an inclination of the predetermined boundary surface, and acquire the boundary surface of the soft tissue, based on a predetermined function including the variation parameter and the smoothness parameter.

Via the slice-based segmentation, the image processing unit may acquire a plurality of cross-section ultrasound images that are perpendicular to the target bone, acquire a boundary line of the soft tissue from each of the plurality of cross-section ultrasound images, and acquire the boundary surface of the soft tissue, based on the boundary line of the soft tissue acquired from each of the plurality of cross-section ultrasound images.

The image processing unit may acquire binary ultrasound image data via thresholding based on the ultrasound image data, distinguish a plurality of segments within the binary ultrasound image data from one another via labeling, determine one of the plurality of segments as a target image, based on image properties of the target bone, and acquire the first information, based on the target image.

The image processing unit may semi-automatically acquire the boundary surface of the soft tissue, based on at least one input received from a user.

According to one or more embodiments of the present invention, an ultrasound diagnosis method includes acquiring ultrasound image data regarding a object including a target bone which is to be diagnosed; acquiring first information about at least one selected from a location of the target bone within an ultrasound image and a length of the target bone, based on volume data included in the ultrasound image data; acquiring a boundary surface of a soft tissue that is adjacent to the target bone, based on the first information; and automatically acquiring a volume of an interior of the boundary surface of the soft tissue.

The ultrasound diagnosis method may further include three-dimensionally rendering at least one selected from the target bone and the boundary surface of the soft tissue, based on the volume data.

The ultrasound diagnosis method may further include displaying the ultrasound image that is based on the ultrasound image data.

The displaying may include displaying at least one selected from: the ultrasound image that is based on a 3D-rendered target bone, a boundary surface of a 3D-rendered soft tissue, a cross section of the 3D-rendered target bone, a cross section of the boundary surface of the 3D-rendered soft tissue, and volume data; a length value of the target bone; and a volume value of the interior of the boundary surface of the soft tissue.

The displaying may include displaying an ultrasound image on which the target bone and the soft tissue are distinguished from each other.

The displaying may include displaying at least one selected from a 3D-rendered target bone, a boundary surface of the 3D-rendered soft tissue, a cross section of the 3D-rendered target bone, and a cross section of the boundary surface of the 3D-rendered soft tissue, with different patterns, different colors, and different degrees of transparency.

The acquiring of the boundary surface of the soft tissue may include acquiring a boundary surface of the soft tissue that surrounds at least a predetermined portion of the target bone.

The acquiring of the boundary surface of the soft tissue may include acquiring the boundary surface of the soft tissue such that a ratio of the length of the target bone to a length of the boundary surface of the soft tissue has a predetermined ratio in a lengthwise direction of the target bone.

The predetermined ratio may include at least one selected from a pre-determined ratio and a ratio received from a user.

The acquiring of the boundary surface of the soft tissue may use at least one selected from an active contour algorithm, segmentation using a cylindrical coordinate system transform, and slice-based segmentation.

The acquiring of the boundary surface of the soft tissue may include, via the active contour algorithm: extending a predetermined boundary surface from the target bone to the boundary surface of the soft tissue on the ultrasound image; acquiring an extension parameter enabling the predetermined boundary surface to extend to the boundary surface of the soft tissue on the ultrasound image; acquiring a suppression parameter having an opposite sign to the extension parameter and preventing the predetermined boundary surface from exceeding the boundary surface of the soft tissue on the ultrasound image; acquiring a smoothness parameter of which an absolute value decreases with a decrease in a change rate of an inclination of the predetermined boundary surface at a predetermined point; and acquiring the boundary surface of the soft tissue, based on a predetermined function including the extension parameter, the suppression parameter, and the smoothness parameter.

The acquiring of the boundary surface of the soft tissue may include, via the segmentation using the cylindrical coordinate system transform: transforming the ultrasound image to a cylindrical coordinate system; extending a predetermined boundary surface from the target bone to the boundary surface of the soft tissue on the ultrasound image; acquiring a variation parameter of which an absolute value decreases with an increase in a luminance change rate of a voxel in an ultrasound image obtained by the transformation to the cylindrical coordinate system; acquiring a smoothness parameter of which an absolute value decreases with a decrease in a change rate of an inclination of the predetermined boundary surface; and acquiring the boundary surface of the soft tissue, based on a predetermined function including the variation parameter and the smoothness parameter.

The acquiring of the boundary surface of the soft tissue may include, via the slice-based segmentation: acquiring a plurality of cross-section ultrasound images that are perpendicular to the target bone; acquiring a boundary line of the soft tissue from each of the plurality of cross-section ultrasound images; and acquiring the boundary surface of the soft tissue, based on the boundary line of the soft tissue acquired from each of the plurality of cross-section ultrasound images.

The acquiring of the first information may include acquiring binary ultrasound image data via thresholding based on the ultrasound image data; distinguishing a plurality of segments within the binary ultrasound image data from one another via labeling; determining one of the plurality of segments as a target image, based on image properties of the target bone; and acquiring the first information, based on the target image.

The acquiring of the boundary surface of the soft tissue may include semi-automatically acquiring the boundary surface of the soft tissue, based on at least one input received from a user.

According to one or more embodiments of the present invention, a non-transitory computer-readable recording medium has recorded thereon a program for executing the ultrasound diagnosis method.

DETAILED DESCRIPTION

Figure 1:
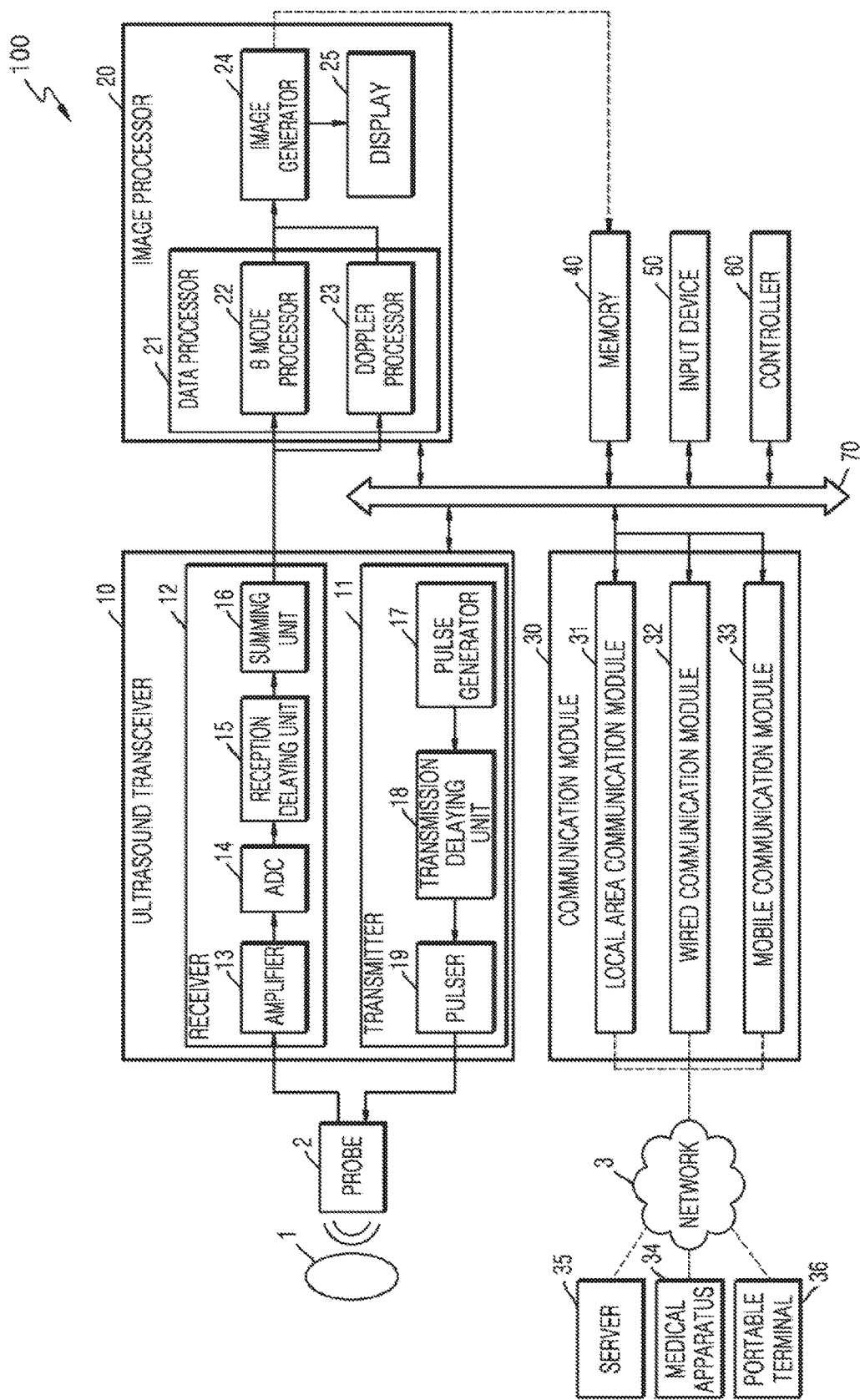
FIG. 1 is a block diagram of an ultrasound diagnosis apparatus according to an exemplary embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments will be described in detail with reference to the accompanying drawings.

FIG. 1 is a diagram illustrating an ultrasound imaging apparatus 100 according to exemplary embodiments.

FIG. 1 illustrates an overall configuration of an ultrasound diagnosis apparatus 100 according to exemplary embodiments.

Referring to FIG. 1, the ultrasound diagnosis apparatus 100 may include a probe 2, an ultrasound transmission/reception unit 10, an image processor 20, a communication module 30, a memory 40, an input device 50, and a control unit 60, where the components stated above may be connected to one another via buses 70.

The ultrasound diagnosis apparatus 100 may be embodied not only as a cart type apparatus, but also as a portable apparatus. Examples of portable ultrasound diagnosis apparatuses may include a picture archiving and communication system (PACS) viewer, a smart phone, a laptop computer, a personal digital assistant (PDA), and a tablet personal computer (PC); however, the inventive concept is not limited thereto.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Also, the probe 2 may be connected to a main body of the ultrasound diagnosis apparatus 100 by wire or wirelessly. According to exemplary embodiments, the ultrasound diagnosis apparatus 100 may include a plurality of probes 2.

A transmitter 11 supplies a driving signal to the probe 2. The transmitter 110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 1124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components 22.

Similarly, a Doppler processor 23 may extract Doppler components from ultrasound data, and the image generator 24 may generate a Doppler image indicating a movement of an object as colors or waveforms based on the extracted Doppler components.

According to an embodiment of the present invention, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound apparatus 100. For example, the memory 40 may store medical data related to diagnosis of an object, such as ultrasound data and an ultrasound image that are input or output, and may also store algorithms or programs which are to be executed in the ultrasound apparatus 100.

The memory 40 may be any of various storage media, e.g., a flash memory, a hard disk drive, EEPROM, etc. Furthermore, the ultrasound apparatus 100 may utilize web storage or a cloud server that performs the storage function of the memory 40 online.

The input device 50 refers to a means via which a user inputs data for controlling the ultrasound diagnosis apparatus 100. The input device 50 may include hardware components, such as a keypad, a mouse, a touch panel, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the input device 50 shown in FIG. 1.

All or some of the probe 2, the ultrasound transceiver 10, the image processor 20, the communication module 30, the memory 40, the input device 50, and the controller 60 may be implemented as software modules. However, embodiments of the present invention are not limited thereto, and some of the components stated above may be implemented as hardware modules. Also, at least one of the ultrasound transmission/reception unit 10, the image processor 20, and the communication module 30 may be included in the control unit 60; however, the inventive concept is not limited thereto.

A marker may be set to indicate a predetermined position or set a diagnosis region in an ultrasound image including an object.

In detail, the marker may be set at a portion that is to be observed in detail by the user to diagnose a disease or to check the health of a patient. The inventive concept provides an ultrasound diagnosis apparatus and an ultrasound image display method, which may change and output an ultrasound image to more accurately diagnose an object region in which the marker is set.

Figure 2:
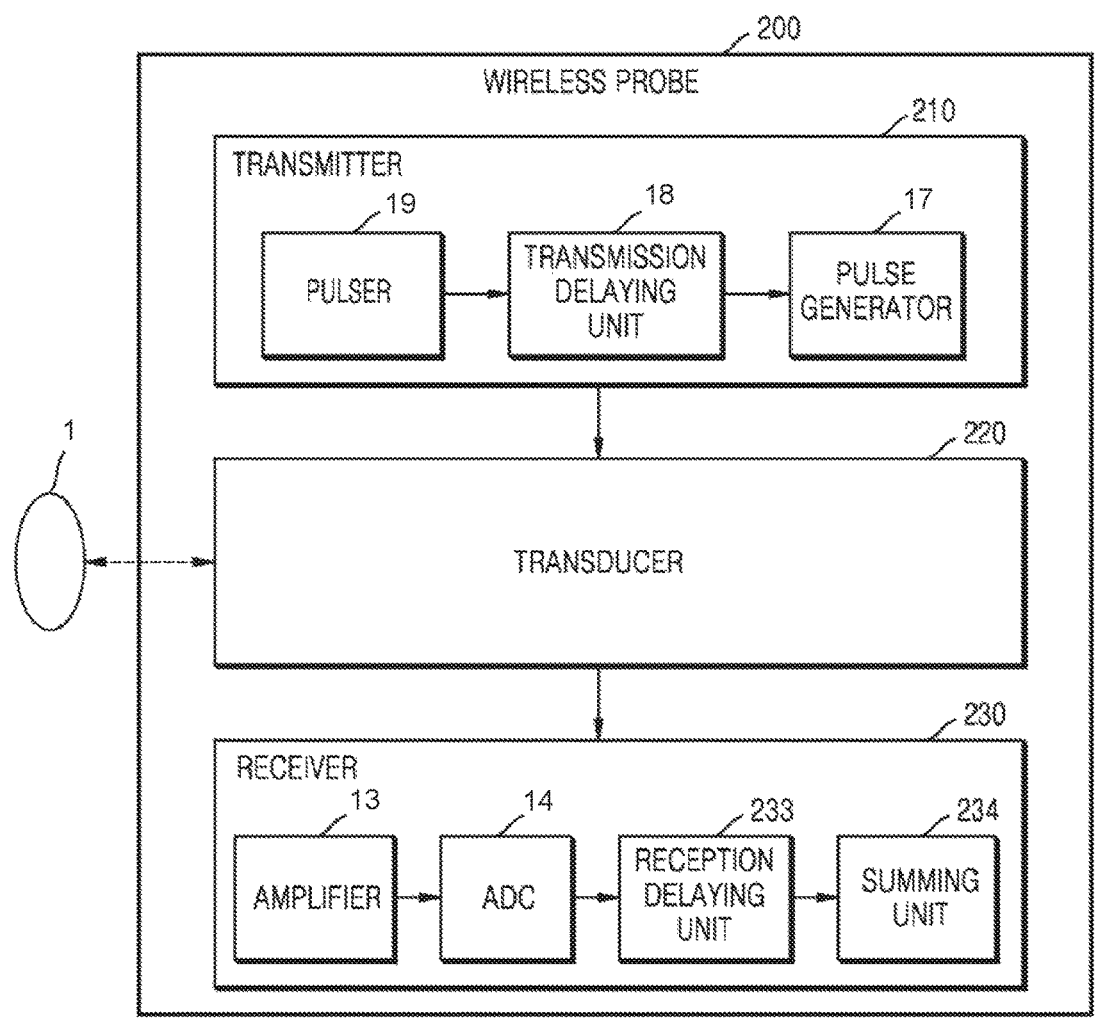
FIG. 2 is a block diagram of a wireless probe according to an exemplary embodiment of the present invention.

FIG. 2 is a block diagram showing a configuration of a wireless probe 200 according to an embodiment of the present invention.

As described above with reference to FIG. 1, the wireless probe 200 may include a plurality of transducers, and, according to embodiments, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments, the wireless probe 200 may selectively include a reception delaying unit 233 and a summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

An ultrasound diagnosis apparatus may be used in fetal biometric measurements. Fetal biometric measurements can be performed to estimate a gestational age of a fetus, evaluate the size of the fetus, and monitor growth of the fetus. Examples of the fetal biometric measurements include volume measurement of a predetermined part of an arm or leg of a fetus. A measured volume of a fetus may be used to estimate a nutrition state of the fetus. Thus, ultrasound diagnosis apparatuses and methods capable of efficiently measuring the volume of an object are required.

An ultrasound diagnosis apparatus and method for measuring the volume of an object, and a computer-readable storage medium having the ultrasound diagnosis method recorded thereon, according to an embodiment of the present invention, will now be described in detail with reference to FIGS. 3-16.

Figure 3:
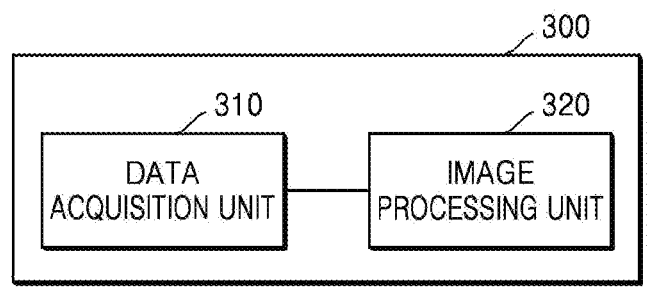
FIG. 3 is a block diagram of an image processing apparatus according to an exemplary embodiment of the present invention.

FIG. 3 is a block diagram of an image processing apparatus according to an embodiment of the present invention.

An ultrasound diagnosis apparatus 300 is any electronic apparatus capable of receiving, processing, and/or outputting an ultrasound image, and may be used for medical imaging apparatuses, such as, an ultrasound imaging apparatus, a computed tomography (CT) apparatus and a magnetic resonance imaging (MRI) apparatus. For example, the ultrasound diagnosis apparatus 300 may be included in a medical imaging apparatus.

Referring to FIG. 3, the ultrasound diagnosis apparatus 300 includes a data acquisition unit 310 and an image processing unit 320. The image processing unit 320 of FIG. 3 may correspond to the image processing unit 20 of FIG. 1.

The data acquisition unit 310 acquires ultrasound image data regarding an object including a target bone which is to be diagnosed. The image processing unit 320 acquires first information about at least one selected from a location of the target bone within an ultrasound image and a length of the target bone, based on volume data included in the ultrasound image data, acquires a boundary surface of a soft tissue that is adjacent to the target bone, based on the first information, and automatically acquires a volume of the interior of the boundary surface of the soft tissue. The image processing unit 320 may semi-automatically acquire the boundary surface of the soft tissue, based on at least one input received from a user. The ultrasound image data means data that is generated based on an ultrasound echo signal acquired via an ultrasound scan, or data that is used to image an ultrasound-scanned object to obtain an ultrasound image.

The image processing unit 320 may three-dimensionally render at least one selected from the target bone and the boundary surface of the soft tissue, based on the volume data. Various methods may be used as the 3D rendering. In addition, the 3D rendering may be performed based on the boundary surface of the soft tissue acquired based on first information.

The data acquisition device 310 may acquire the ultrasound image data regarding the object. The object is an animal body including a human body, or a part of the animal body. The object includes a target bone, and the target bone has a long tube shape. For example, the object is a pregnant woman, and the target bone may be a long bone of a fetus, such as a thighbone. The object may include a soft tissue that is adjacent to the target bone. The soft tissue denotes a soft pat that surrounds a bone or a joint, or the tissue of the soft part. For example, the soft tissue may include a film, a tendon, a ligament, fat, and a skin tissue that cover a bone. The ultrasound image data may be an ultrasound image of the target bone, 2D ultrasound image data used to image a section of the object, or volume data used to three-dimensionally image a 3D space within the object.

The 2D ultrasound image data may be a plurality of pixel values, and the volume data may be a plurality of voxel values. A pixel value may be a luminance value of a pixel corresponding to the pixel value, and a voxel value may be a luminance value of a voxel corresponding to the voxel value. For convenience of explanation, hereinafter, a point is used as a term that means a pixel or a voxel.

The data acquisition unit 310 may acquire the ultrasound image data by scanning the object by using an ultrasound signal or the like, but embodiments of the present invention are not limited thereto. For example, the data acquisition unit 310 may correspond to the ultrasound transmission/reception unit 10 of FIG. 1, and may receive an ultrasound echo signal transmitted by the probe 2 and acquire the ultrasound image data by using the received ultrasound echo signal. As another example, the data acquisition unit 310 may receive scan information obtained by scanning the object by using a scanner outside the ultrasound diagnosis apparatus 300, for example, ultrasound data into which an ultrasound echo signal is converted, and acquire the ultrasound image data based on the scan information. As another example, the data acquisition unit 310 may receive the ultrasound image data from an external apparatus. However, embodiments of the present invention are not limited thereto, and the ultrasound diagnosis apparatus 300 may acquire the ultrasound image data according to any of various methods.

The image processing unit 320 may acquire at least one selected from a location of the target bone, a length thereof, and a volume of the interior of the boundary surface of the soft tissue, by processing the ultrasound image data. The image processing unit 320 may acquire binary image data via thresholding based on the ultrasound image data, distinguish a plurality of segments within the binary ultrasound image data via labeling, determine one of the plurality of segments as a target image, based on image properties of the target bone, and measure at least one selected from a location and a length of the target bone, based on the target image.

Figure 4:
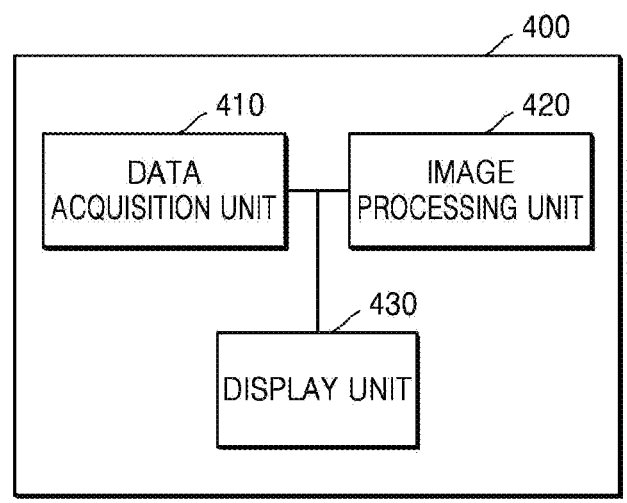
FIG. 4 is a block diagram of an image processing apparatus according to an exemplary embodiment of the present invention.

FIG. 4 is a block diagram of an image processing apparatus according to an embodiment of the present invention.

Referring to FIG. 4, an ultrasound diagnosis apparatus 400 includes a data acquisition unit 410, an image processing unit 420, and a display unit 430. Since the data acquisition unit 410 and the image processing unit 420 of FIG. 4 are respectively the same as the data acquisition unit 310 and the image processing unit 320 of FIG. 3, redundant descriptions thereof are omitted here.

The display unit 430 of FIG. 4 may correspond to the display unit 25 of FIG. 1. The display unit 430 may display various ultrasound images that are generated by the image processing unit 420. The display unit 430 may also display at least one selected from: an ultrasound image that is based on a 3D-rendered target bone, a boundary surface of a 3D-rendered soft tissue, a cross section of the 3D-rendered target bone, a cross section of the boundary surface of the 3D-rendered soft tissue, and volume data; a length value of the target bone; and a volume value of the interior of the boundary surface of the soft tissue.

The display unit 430 may also display an ultrasound image on which the target bone and the soft tissue are distinguished from each other. For example, the display unit 430 may display at least one selected from the 3D-rendered target bone, the boundary surface of the 3D-rendered soft tissue, the cross section of the 3D-rendered target bone, and the cross section of the boundary surface of the 3D-rendered soft tissue, with different patterns, different colors, and different degrees of transparency.

Figure 5A:
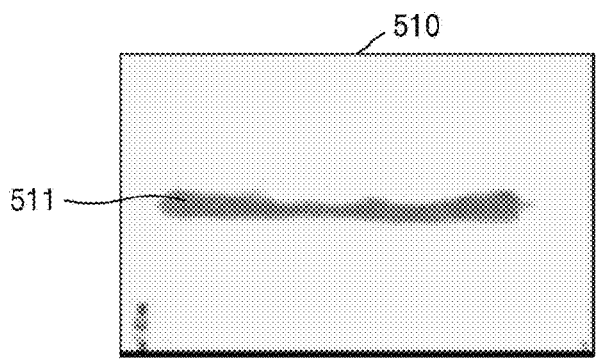
FIGS. 5A-5D illustrate images that may be displayed on a display unit, according to an exemplary embodiment of the present invention.
Figure 5B:
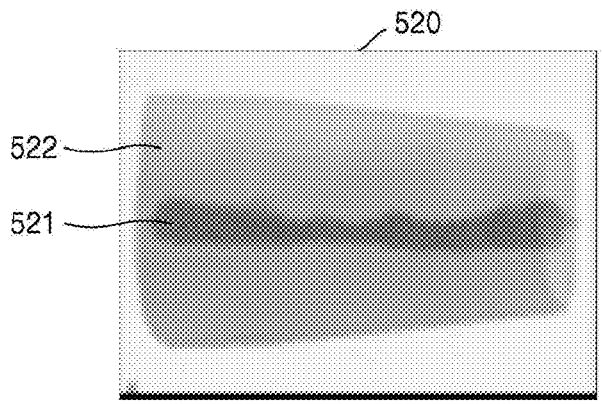

FIGS. 5A-7 and 17 illustrate images that may be displayed on the display unit 430, according to an embodiment of the present invention. The image processing unit 420 may three-dimensionally render at least one selected from the target bone and the boundary surface of the soft tissue, based on the volume data. The display unit 430 may display an image 510 including a 3D-rendered target bone 511, as shown in FIG. 5A. The display unit 430 may display an image 520 including both a 3D-rendered target bone 521 and a boundary surface 522 of a 3D-rendered soft tissue, as shown in FIG. 5B.

Figure 5C:
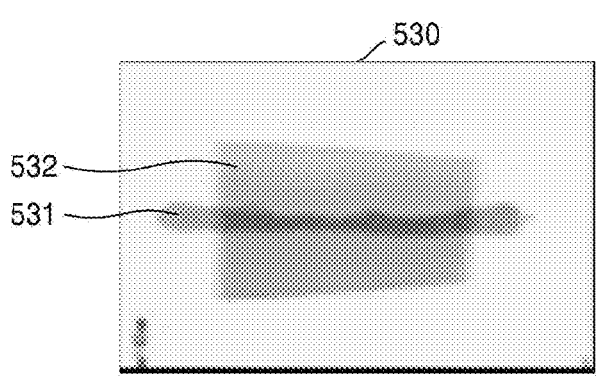

The boundary surface 522 of the soft tissue may surround at least a predetermined portion of the 3D-rendered target bone 521. The boundary surface 522 of the soft tissue and the target bone 521 may have the same horizontal length as shown on the image 520 of FIG. 5B, but embodiments of the present invention are not limited thereto. The boundary surface 522 of the soft tissue may have a horizontal length that is greater than that of the 3D-rendered target bone 521. For example, as shown in FIG. 5C, a boundary surface 532 of a soft tissue may have a horizontal length that is less than that of a target bone 531.

Figure 5D:
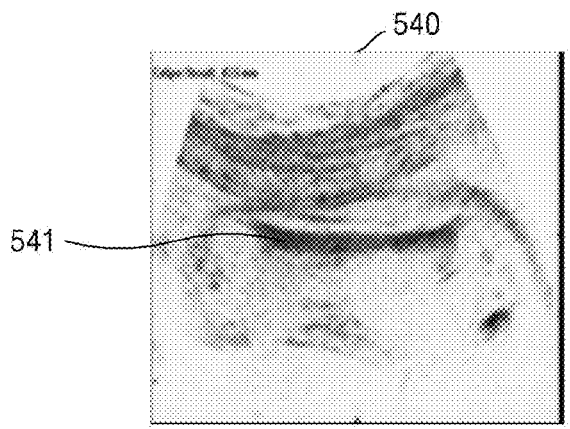

The display unit 430 may display at least one selected from ultrasound images that are based on the volume data. For example, as shown in FIG. 5D, the display unit 430 may display an image 540 showing a target bone 541.

Figure 6A:
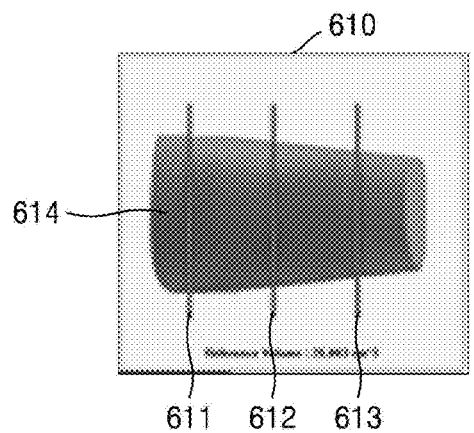
FIGS. 6A-6C illustrate images that may be displayed on a display unit, according to an exemplary embodiment of the present invention.

Referring to FIG. 6A, the display 430 may display an image 610 including a boundary surface 614 of a 3D-rendered soft tissue. The boundary surface 614 of a 3D-rendered soft tissue may display locations 611, 612 and 613 of longitudinal sections.

Figure 6B:
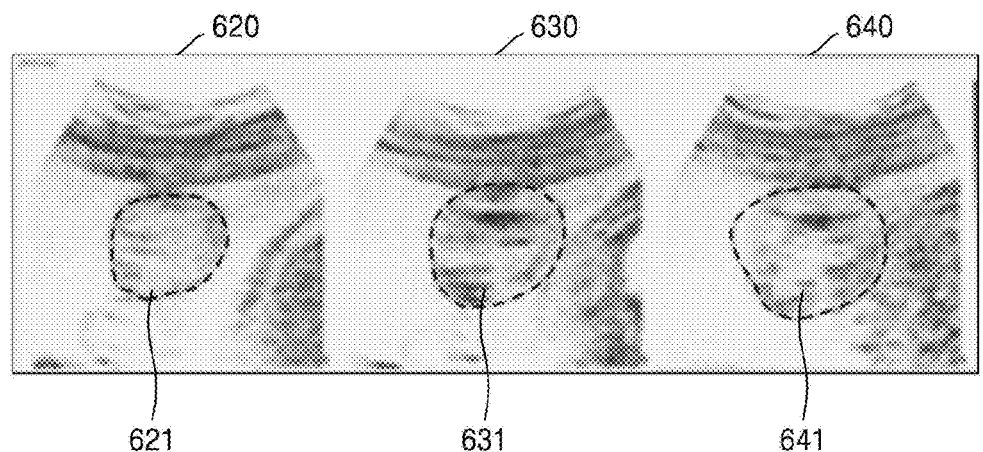

Referring to FIG. 6B, the display unit 430 may display ultrasound images 620, 630, and 640 obtained at the locations 611, 612 and 613 of the longitudinal sections. For example, the display unit 430 may display the ultrasound image 620 obtained at the location 613 of the longitudinal section. A boundary line 621 of the soft tissue 621 may be displayed on the ultrasound image 620. The boundary line 621 of the soft tissue may be marked by a dotted line, a solid line, or the like. The display unit 430 may display the ultrasound image 630 obtained at the location 612 of the longitudinal section. A boundary line 631 of the soft tissue may be displayed on the ultrasound image 630. The boundary line 631 of the soft tissue may be marked by a dotted line, a solid line, or the like. The display unit 430 may display the ultrasound image 640 obtained at the location 611 of the longitudinal section. A boundary line 641 of the soft tissue may be displayed on the ultrasound image 640. The boundary line 641 of the soft tissue may be marked by a dotted line, a solid line, or the like. A user may easily ascertain the boundary surface of the soft tissue from the ultrasound images 620, 630 and 640 displayed on the display unit 430.

Figure 6C:
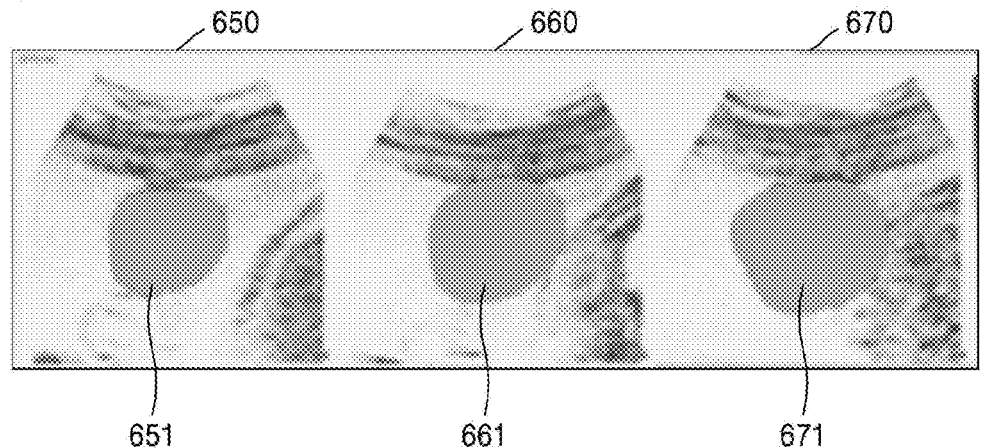

Referring to FIG. 6C, the display unit 430 may display ultrasound images 650, 660, and 670 obtained at the locations 611, 612 and 613 of the longitudinal sections. In contrast with FIG. 6B, the display unit 430 may display the interiors of boundary lines 651, 661 and 671 of a soft tissue with a particular color. A user may easily ascertain the boundary surface of the soft tissue from the ultrasound images 650, 660 and 670 displayed on the display unit 430.

Figure 7:
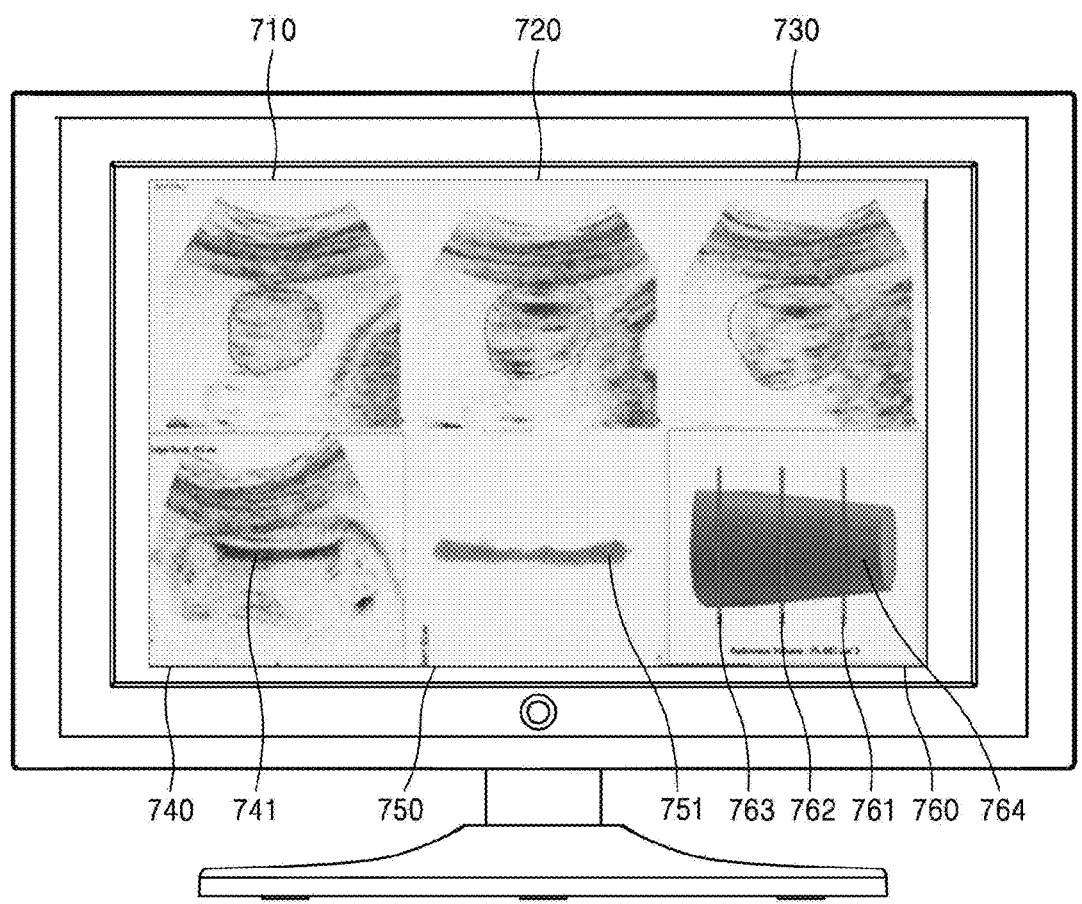
FIG. 7 illustrates images that may be displayed on a display unit, according to an exemplary embodiment of the present invention.

Referring to FIG. 7, the display 430 may display a combination of the images shown in FIGS. 5A-6C on one screen image. For example, the display unit 430 may display an image 760 including a boundary surface 764 of a 3D-rendered soft tissue. The display unit 430 may display the boundary surface 764 of the 3D-rendered soft tissue including locations 761, 762 and 763 of longitudinal sections. The display unit 430 may also display ultrasound images 710, 720, and 730 obtained at the locations 761, 762, and 763 of the longitudinal sections. The display unit 430 may also display an image 750 including a 3D-rendered target bone 751. The display unit 430 may also display an ultrasound image 740 including a target bone 741. The screen image illustrated in FIG. 7 is exemplary, and the display unit 430 may display various images in various combinations.

Figure 17:
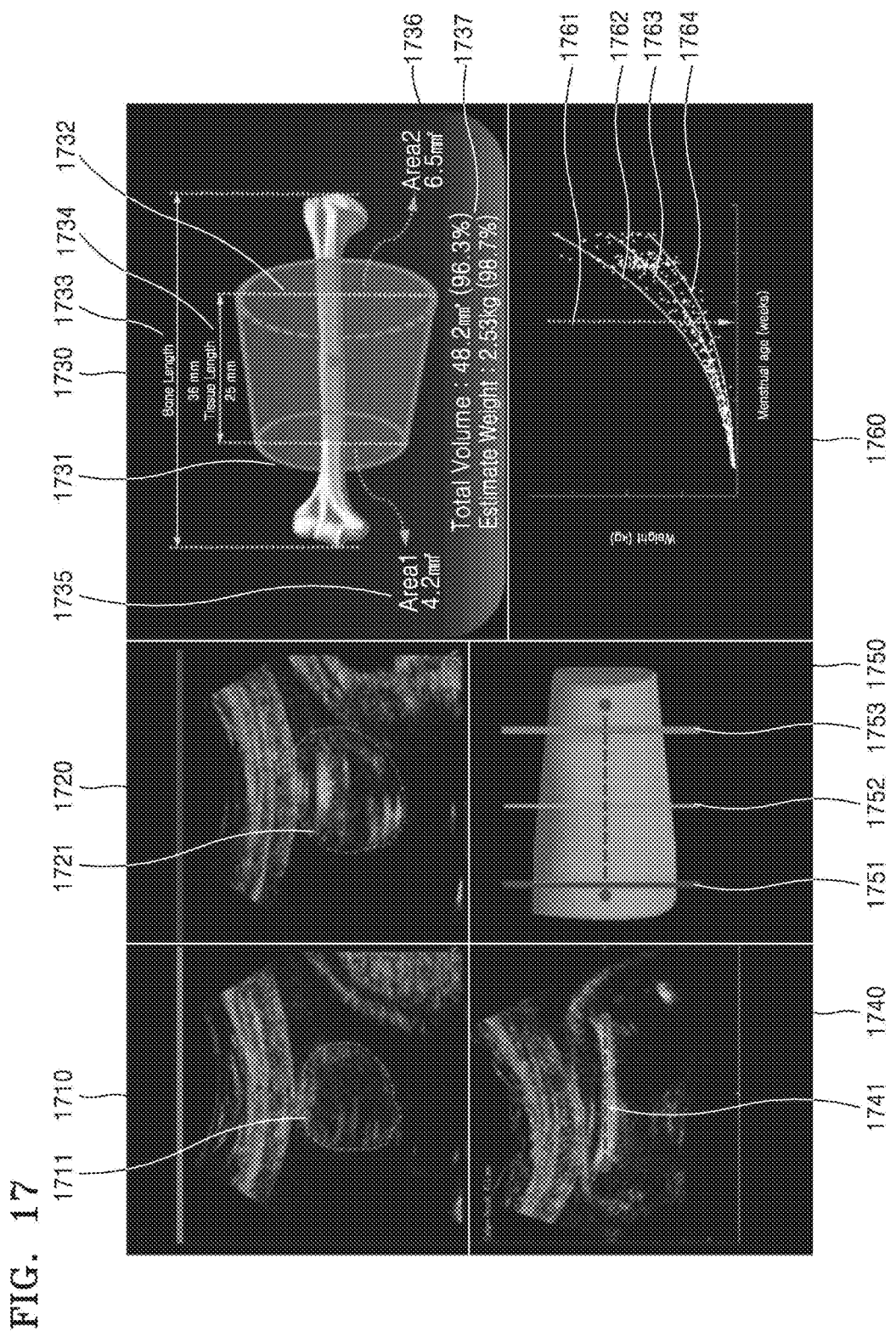
FIG. 17 illustrates images that may be displayed on a display unit, according to an exemplary embodiment of the present invention.

Referring to FIG. 17, the display 430 may display an ultrasound image 1740 including a target bone. The ultrasound diagnosis apparatus 400 may acquire a length and a location of the target bone. The display unit 430 may also display an indicator 1741 of the target bone, together with the ultrasound image 1740, based on the acquired length and location of the target bone. For example, the indicator 1741 may be formed of both ends of the target bone and a dotted line that connects both ends of the target bone to each other. A user may easily ascertain the location and length of the target bone, based on the indicator 1741.

The display unit 430 may also display an image 1750 including a boundary surface of a 3D-rendered soft tissue. The indicator 1741 displayed on the ultrasound image 1740 may also be displayed on the image 1750. The display unit 430 may also display a boundary surface 1750 of a 3D-rendered soft tissue including locations 1751, 1752, and 1753 of longitudinal sections. According to an embodiment of the present invention, the locations 1751, 1752, and 1753 of longitudinal sections may be determined by a user. According to another embodiment of the present invention, the locations 1751, 1752, and 1753 of longitudinal sections may be automatically determined by the ultrasound diagnosis apparatus 400.

For example, according to an embodiment of the present invention, the ultrasound diagnosis apparatus 400 may determine both ends and a center point of the target bone, as the locations 1751, 1752, and 1753 of longitudinal sections. According to another embodiment of the present invention, the ultrasound diagnosis apparatus 400 may previously store a predetermined ratio. For example, the previously stored predetermined ratio may be 50%. The ultrasound diagnosis apparatus 400 may determine a center point of the target bone and points that are quarter lengths (25%) of the target bone from the center point of the target bone, as longitudinal section points.

The display unit 430 may display ultrasound images obtained at the locations 1751, 1752, and 1753 of the longitudinal sections. For example, the ultrasound image 1720 obtained at the location 1751 of the longitudinal section on the image 1750 may be displayed. The ultrasound image 1710 obtained at the location 1753 of the longitudinal section on the image 1750 may also be displayed. Boundaries 1711 and 1721 of a soft tissue may be displayed on the ultrasound images 1710 and 1720, respectively.

The display unit 430 may display an image 1730 including a boundary surface of a 3D-rendered soft tissue. A length value 1733 of the target bone may be displayed on the image 1730. The length value 1733 of the target bone may be, for example, 36 mm. A length value of the soft tissue may also be displayed on the image 1730. For example, the length value of the soft tissue may be 25 mm. Width values 1735 and 1736 of cross sections of the soft tissue may also be displayed on the image 1730. For example, the width values 1735 and 1736 of the cross sections may be respectively 4.2 mm$^2$ and 6.5 mm$^2$. A volume of the interior of the boundary of the soft tissue and an estimated weight based on the volume are indicated by reference numeral 1737, and may also be displayed on the image 1730. For example, the volume of the interior of the boundary of the soft tissue may be 48.2 mm$^3$, and the estimated weight may be 2.53 kg. Reliabilities of the volume and the estimated weight may also be displayed on the image 1730, and may be respectively 96.3% and 98.7%.

The display unit 430 may display a statistical graph 1760 showing an estimated weight versus a menstrual age. The statistical graph 1760 may show a current menstrual age 1761. A maximum graph 1762, an intermediate graph 1763, and a minimum graph 1764 of the estimated weight according to the menstrual age may also be displayed on the statistical graph 1760. A user may easily obtain desired information, based on information displayed on the display unit 430 as described above.

A method of acquiring at least one selected from a location and a length of a target bone when ultrasound image data is 2D ultrasound image data will now be described in connection with the ultrasound diagnosis apparatus 400 of FIG. 4, with reference to FIGS. 8A-9.

FIGS. 8A-8G illustrate 2D images obtained from 2D ultrasound image data, according to an embodiment of the present invention.

Figure 8A:
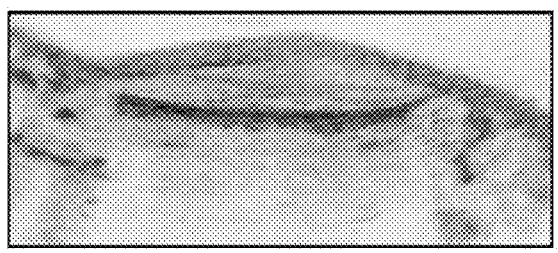
FIGS. 8A-8G illustrate 2D images obtained from 2D ultrasound image data, according to an exemplary embodiment of the present invention.

FIG. 8A illustrates a 2D image obtained from 2D ultrasound image data.

The 2D image of FIG. 8A is a B mode ultrasound image.

Referring to FIG. 8A, the 2D image includes a target image which is an image of a target bone. However, due to noise and an image of a tissue around the target bone, a boundary of the target image is not distinct from the 2D image. Thus, before performing thresholding, the image processing unit 420 may process the 2D image as follows.

The image processing unit 420 may acquire a preprocessed image by preprocessing the 2D image. For example, denoising based on a total variation (TV) algorithm may be performed as preprocessing.

Figure 8B:
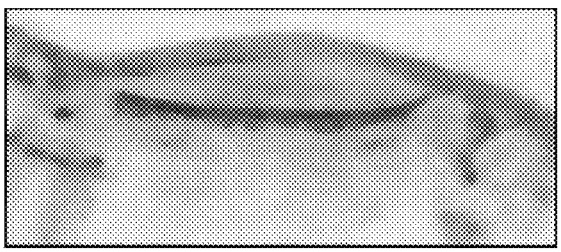

FIG. 8B illustrates a pre-processed image obtained via denoising. Referring to FIG. 8B, noise is removed via denoising, and an edge of the target image is maintained.

Denoising based on a TV algorithm is just an example, and the image processing unit 420 may remove noise from the 2D image via any of various other preprocessing methods in order to improve the quality of an image. However, the image processing unit 420 may skip preprocessing.

The target image, which is an image of the target bone, is thin and long, and a brightness value of the target image is higher than those of the other areas. Thus, to extract a thin, long, and bright area from the preprocessed image, the image processing unit 420 may perform a top-hat conversion on the preprocessed image. When preprocessing is omitted, the image processing unit 420 may perform a top-hat conversion on a binary image.

A top-hat conversion h may be expressed as Equation 1:

$$h = f - (f \circ b)$$ [Equation 1]

where f indicates an input image, namely, a preprocessed image, b indicates a structuring element, ∘ indicates an opening operation, and h indicates a top-hat converted image.

Figure 8C:
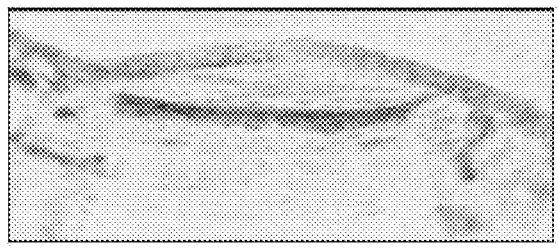

FIG. 8C illustrates a top-hat converted image.

To more clearly distinguish the target image from the other areas by making the edge of the target image more distinct, contrast enhancing may be performed on the top-hat converted image, after a top-hat conversion is performed.

For example, an image CEh(p) (where p indicates a point) obtained by applying contrast enhancing to a top-hat converted image of a 256 gray level may be acquired using Equation 2:

$$CEh(p) = \left(\frac{h(p) - \min}{\max - \min}\right) \times 255$$ [Equation 2]

where h(p) indicates a luminance value of the point p in the top-hat converted image, and max and min respectively indicate a maximum luminance value and a minimum luminance value in the top-hat converted image. Since min is 0 or is approximate to 0, an adequately small value, such as, min=20, may be allocated. In Equation 2, '255' varies according to a gray level that is applied to an image. When the gray level applied to an image is k, a value of (k−1) may be applied instead of '255' of Equation 2.

Figure 8D:
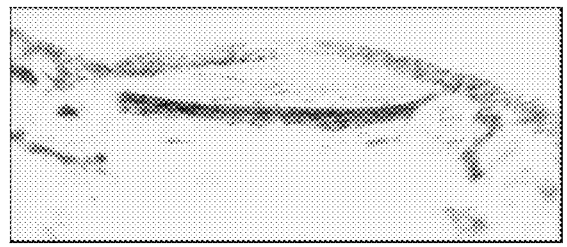

FIG. 8D illustrates a contrast-enhanced image.

As such, the image processing unit 420 may perform denoising, a top-hat conversion, and contrast enhancement on the 2D image.

Next, the image processing unit 420 may acquire a binary image to which an adaptive threshold has been applied, from the contrast-enhanced image.

For example, a binary image g(p) may be acquired from the contrast-enhanced image CEh(p) by using Equation 3:

$$g(p) = \begin{cases} 1, & CEh(p) > T \\ 0, & CEh(p) \leq T \end{cases}$$ [Equation 3]

where T indicates an adaptive threshold. In other words, the binary image may be an image in which a point of the contrast-enhanced image having a luminance value that is greater than the adaptive threshold T is displayed with white, and the other points are displayed with black. For example, as for ultrasound images, a bone may be imaged with a bright color, and tissues other than the bone may be imaged with dark colors. Thus, based on a difference between luminance values of a bone and a tissue other than the bone within an image, an ultrasound image may be converted into a binary image capable of distinguishing the bone and the tissue other than the bone.

The adaptive threshold may be acquired based on a mean and a standard deviation of luminance values in the contrast-enhanced image. For example, the adaptive threshold T may be acquired using Equation 4:

$$T = m + a \cdot s$$ [Equation 4]

where m indicates a mean of luminance values in the contrast-enhanced image, s indicates a standard deviation of the luminance values, and a indicates a weight.

Figure 8E:
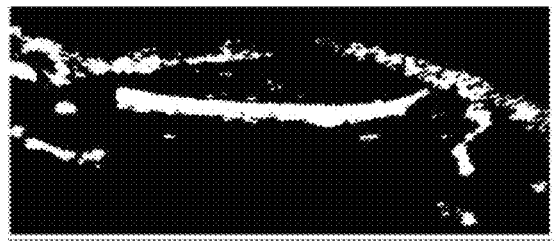

FIG. 8E illustrates a binary image.

Referring to FIG. 8E, the binary image may include the target image, but may also include an image of another tissue having another shape.

Thus, an image processing unit 420 of FIG. 4 may process the binary image as follows, in order to extract the target image.

The image processing unit 420 may distinguish a plurality of segments within binary ultrasound image data from one another via labeling. Each of the plurality of segments is an area in which points having luminance values of 1 are collected. The plurality of segments are candidates of the target image.

Figure 8F:
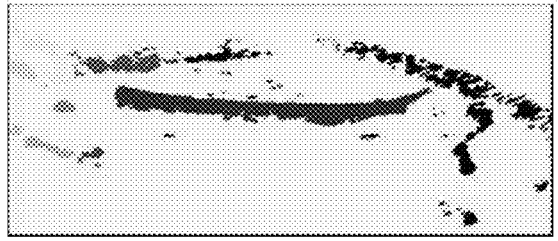

FIG. 8F illustrates a labeled binary image.

Referring to FIG. 8F, a plurality of segments in a binary image are labeled with different gray levels. However, FIG. 8F is only an example of labeling, and the binary image may be labeled according to various other methods. For example, the plurality of segments may be each labeled with a number.

Next, the image processing unit 420 may determine one of the plurality of segments as the target image, based on image properties of the target bone. A segment having a largest number of image properties of the target bone from among the plurality of segments is determined as the target image, which is an image of the target bone.

Since the target bone has a high reflectivity compared with neighboring tissues, the image of the target bone has a luminance value that is greater than those of the other areas. Thus, the image processing unit 420 may determine a segment having the greatest luminance value from among the plurality of segments as the target image. In detail, the image processing unit 420 may obtain a sum of luminance values of the points included in each of the plurality of segments, and determine a segment having the largest sum of luminance values as the target image.

A sum $S_L$ of luminance values of each segment may be calculated using Equation 5:

$$S_L = \Sigma_{p \in L} CEh(p)$$ [Equation 5]

where L indicates an index of a segment and p indicates a point.

When the target image is determined, the image processing unit 420 may display all segments other than the segment determined as the target image, in black.

Figure 8G:
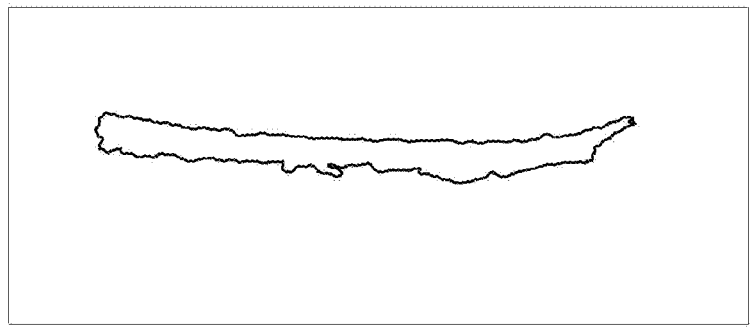

FIG. 8G illustrates a binary image on which only the target image is displayed.

The image processing unit 420 of FIG. 4 may measure a length of the target bone, based on the determined target image.

Figure 9:
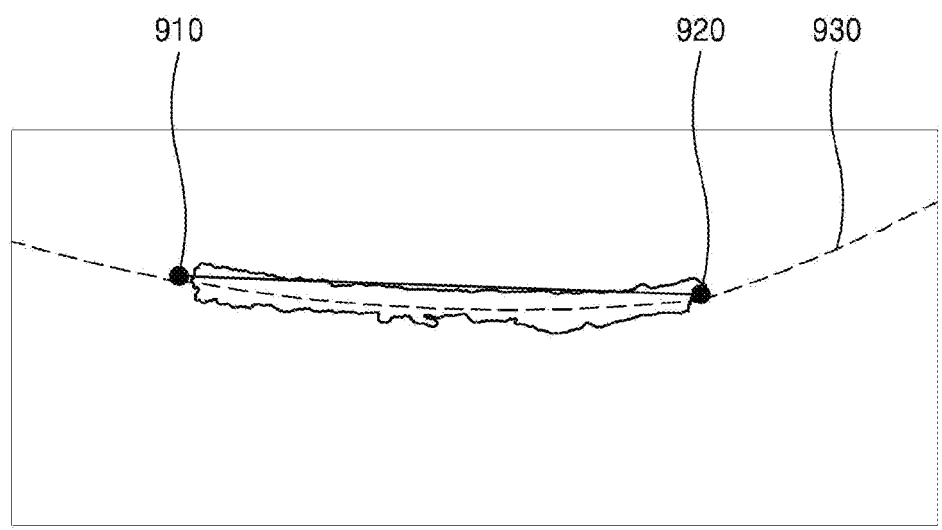
FIG. 9 illustrates a method of measuring the length of a target bone, based on a target image, according to an exemplary embodiment of the present invention.

FIG. 9 illustrates a method of measuring the length of the target bone, based on the target image, according to an embodiment of the present invention.

Referring to FIG. 9, the image processing unit 420 may acquire a measurement line 930 by skeletonizing the target image. The image processing unit 420 may measure the length of the target bone, based on a distance between a first point 910 and a second point 920, which are intersection points of the target image and the measurement line 930.

However, FIG. 9 is only an example, and the image processing unit 420 may detect the first and second points 910 and 920, which are both end points in a long-axis direction of the target image, from the target image according to any of various other methods and measure the length of the target bone based on the distance between the both end points 910 and 920.

Until now, a case where ultrasound image data is 2D ultrasound image data has been described. Hereinafter, a case where ultrasound image data is volume data will be described in connection with the ultrasound diagnosis apparatus 400 of FIG. 4.

Figure 10:
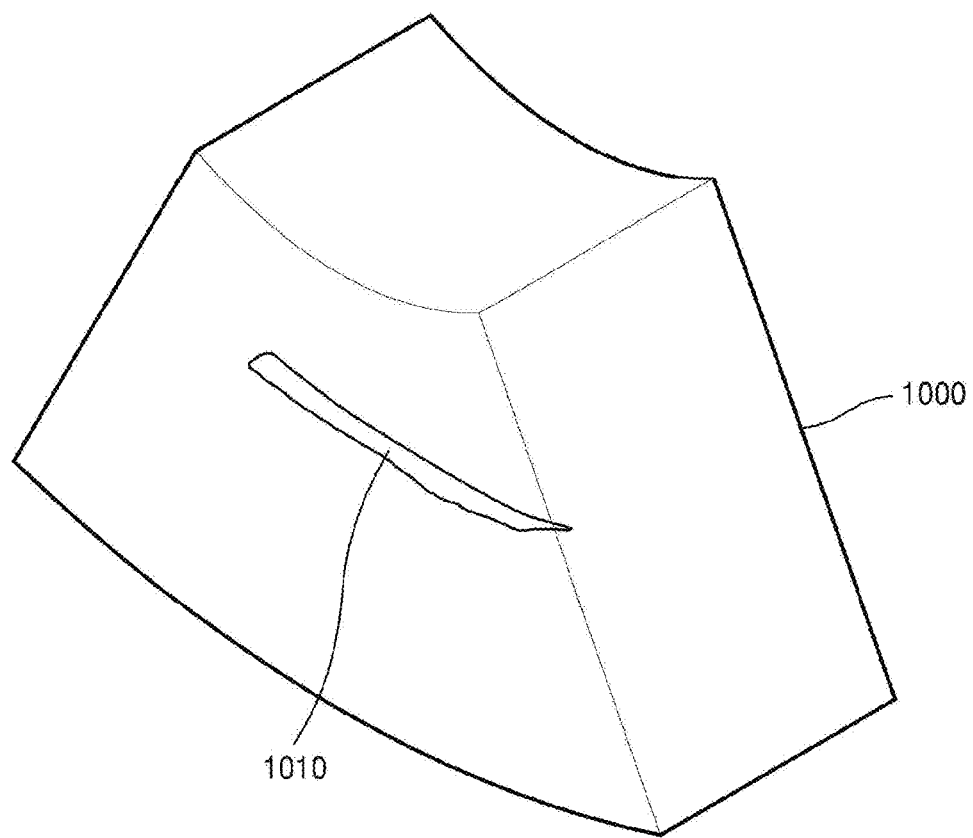
FIG. 10 illustrates volume data according to an exemplary embodiment of the present invention.

FIG. 10 illustrates volume data 1000 according to an embodiment of the present invention.

Referring to FIG. 10, the volume data 1000 includes a target image 1010, which is a 3D image of a target bone. For convenience of illustration, FIG. 10 clearly illustrates the target image 1010, but a boundary of a target image may not be distinct due to noise or the like in actual volume data.

Pixel values are processed in 2D ultrasound image data, whereas voxel values are processed in volume data. Except for this difference, a method of processing 2D ultrasound image data may also be applied to volume data. Thus, portions of a volume data processing method that are the same as the method of processing 2D ultrasound image data will be described briefly, and portions of the volume data processing method that are applied to only volume data will be focused.

The image processing unit 420 may acquire binary volume data from the volume data via thresholding. The above-described top-hat conversion, contrast enhancement, and the like may be performed before the binary volume data is acquired, and then the adaptive threshold may be applied.

The binary volume data may include the target image, but may include an image of a tissue having a different shape from the target image. Thus, image processing for extracting the target image from the binary volume data may be performed as follows.

The image processing unit 420 may perform labeling on the binary volume data. The binary volume data is divided into a plurality of segments via the labeling, and each of the plurality of segments is a 3D area where points having luminance values of 1 are collected. The plurality of segments are candidates of the target image.

The image processing unit 420 may determine one of the plurality of segments as the target image. A segment having a largest number of image properties of the target bone from among the plurality of segments is determined as the target image. A location of the target image within an ultrasound image that is based on the volume data may correspond to a location of the target bone.

Image properties of the target bone may include shape information and a luminance value.

The image processing unit 420 may analyze the shape of each of the plurality of segments and acquire a plurality of residual segments from the plurality of segments based on the analyzed shapes. Next, the image processing unit 420 may determine one of the plurality of residual segments as the target image, based on the luminance value. The location of the target image within the ultrasound image based on the volume data may correspond to the location of the target bone.

Figure 11A:
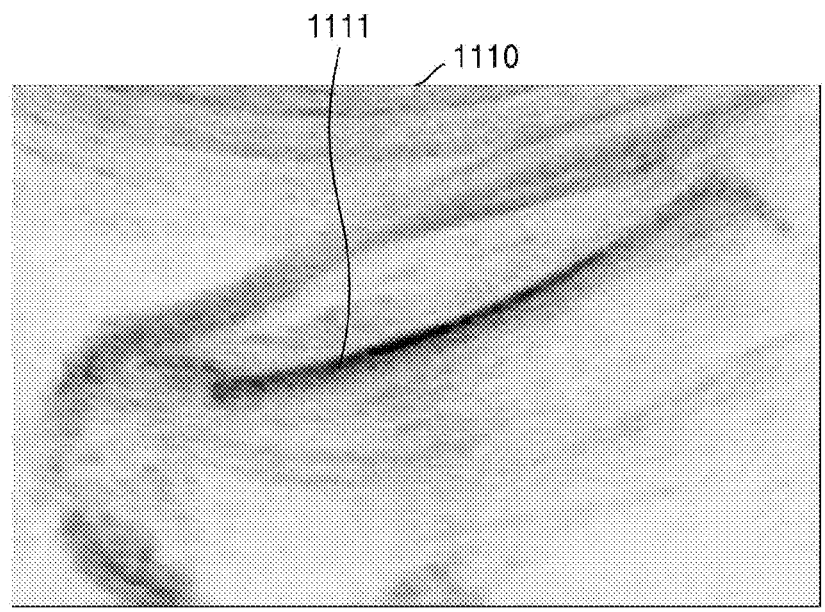
FIGS. 11A and 11B illustrate various shapes of target images according to an exemplary embodiment of the present invention.
Figure 11B:
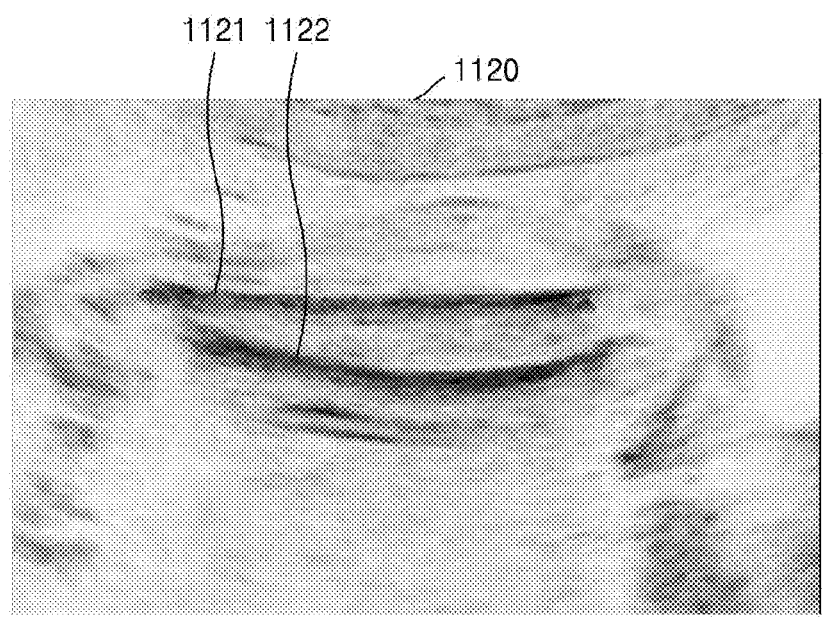

FIGS. 11A and 11B illustrate various shapes of target images 1110 and 1120 according to an embodiment of the present invention.

Referring to FIGS. 11A and 11B, the target images 1110 and 1120 each have a rectilineal tube shape or a curved tube shape. In detail, FIG. 11A illustrates a case where a target bone 1111 included in the target image 1110 has a long tube shape. FIG. 11B illustrates a case where the target image 1120 includes two target bones 1121 and 1122 and the two target bones 1121 and 1122 each have a long tube shape and are parallel to each other.

To analyze the shape of each of the plurality of segments, the image processing unit 420 may perform principle component analysis (PCA) on each of the plurality of segments.

PCA is a technique of analyzing a data collection, and is useful for ascertaining a distribution shape of data. PCA is an analysis technique of finding a direction of maximizing variance of data and contracting the data to thereby express information of the data for easier viewing of information of the data. In PCA, data is linearly transformed to a new coordinate system, like the case where, when data is mapped to a single axis, an axis where variance of the data is the greatest is a first coordinate axis, and an axis where variance of the data is the next greatest is a second coordinate axis.

The image processing unit 420 may obtain a direction and a size of a first principal component, those of a second principal component, and those of a third principal component, for each of the plurality of segments, via PCA. In tube-shaped data, the size of the first principal component is relatively high, and the sizes of the second and third principal components are relatively low. Thus, the image processing unit 420 may analyze the shape of each of the plurality of segments, based on the sizes of the first, second, and third principal components.

Using the sizes of first, second, and third principal components, a tube-score may be defined as follows:

$$Ts = 1 - \frac{\lambda_2 \lambda_3}{\lambda_1^2}$$ [Equation 6]

where Ts indicates the tube score, $\lambda_1$ indicates the size of the first principal component, $\lambda_2$ indicates the size of the second principal component, and $\lambda_3$ indicates the size of the third principal component.

The image processing unit 420 may obtain a tube score for each of the plurality of segments and determine, as the plurality of residual segments, segments having tube cores that are greater than a critical value from among the plurality of segments. In other words, a segment having a tube core that is less than or equal to the critical value is excluded from a candidate of the target image. The critical value may be set empirically. For example, the critical value may be set to be 0.997.

The image processing unit 420 acquires a plurality of residual segments from the plurality of segments, based on the analyzed shapes, and determines one of the plurality of residual segments as the target image, based on the luminance value.

The image processing unit 420 may determine a segment having the greatest luminance value from among the plurality of residual segments as the target image. In detail, the image processing unit 420 may obtain a sum of luminance values of the points included in the plurality of residual segments and determine a segment having the greatest luminance value sum as the target image. A location of the target image within an ultrasound image based on the volume data may correspond to a location of the target bone.

The image processing unit 420 excludes some of the plurality of segments from a candidate of the target image, by analyzing the shapes of the plurality of segments, before the target image is determined. To this end, a segment having a relatively large size may be prevented from being selected as the target image.

The binary volume data may include images of a plurality of long bones. For example, referring to FIG. 11B, a long bone 1121 and another long bone 1122 exist within the volume data. According to the above-described method, the image processing unit 420 may acquire at least one selected from a location and a length of the long bone 1121, namely, the target bone. Next, the image processing unit 420 may select an image of the other long bone 1122 from among the images of the plurality of long bones based on the length of the target bone, and also acquire at least one selected from locations and lengths of the other long bones.

Next, a method of measuring the length of the target bone based on the determined target image will be described.

The image processing unit 420 may determine a longitudinal section of the target image, and measure the length of the target bone, based on the longitudinal section. To accurately measure the length of the target bone, the length of the target bone needs to be measured from the longitudinal section of the target bone.

At least three points are needed to determine a specific plane in a 3D space, and should not be in a straight line. Thus, to determine the longitudinal section of the target image, at least three points on the longitudinal section need to be determined. Next, a method of determining three points on the longitudinal section of the target image will be described with reference to FIG. 12.

Figure 12:
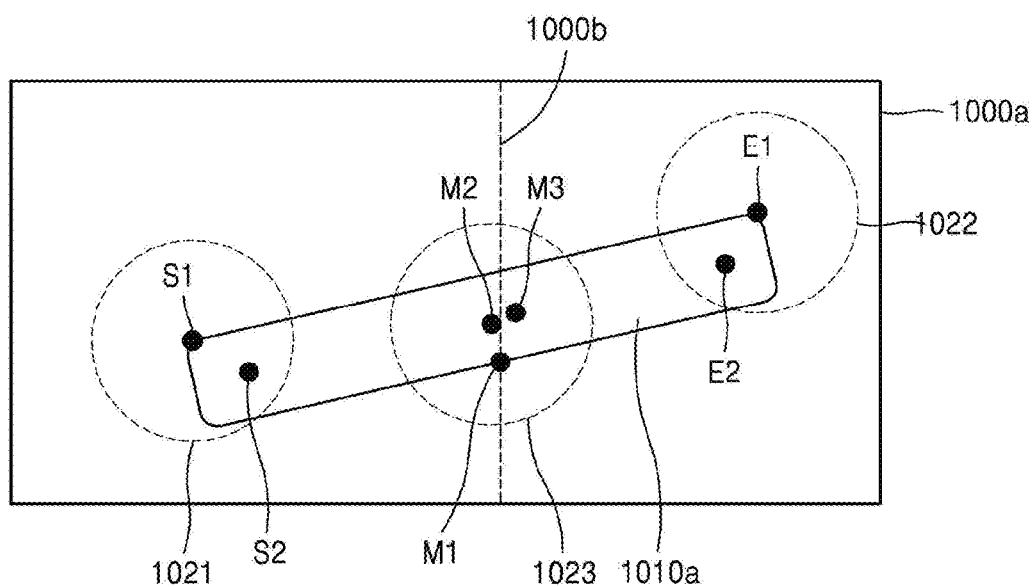
FIG. 12 illustrates a cross section of volume data according to an exemplary embodiment of the present invention.

FIG. 12 illustrates a cross section of volume data 1000a according to an embodiment of the present invention.

Referring to FIG. 12, the volume data 1000a includes a segment that is determined as a target image 1010a. The image processing unit 420 acquires a mean point M1 corresponding to a mean coordinate of all points that belong to the target image 1010a. In a 3D volume data, the mean coordinate may be calculated using Equation 7:

$$X\text{avg} = (X1 + X2 + \ldots + Xn)/n$$

$$Y\text{avg} = (Y1 + Y2 + \ldots + Yn)/n$$

$$Z\text{avg} = (Z1 + Z2 + \ldots + Zn)/n \quad \text{[Equation 7]}$$

where Xavg, Yavg, and Zavg indicate mean coordinate values, n indicates the number of points, and Xn, Yn, and Zn indicate respective coordinate values of the points.

The image processing unit 420 may acquire both end points S1 and E1 that are farthest from a longitudinal section 1000b that passes through the mean point M1 from among points that belonging to the target image 1010a. The longitudinal section 1000b is a longitudinal section of the volume data 1000a that passes through the mean point M1.

The image processing unit 420 sets spheres 1021 and 1022 of which centers are respectively the both end points S1 and E1. The image processing unit 420 acquires a first point S2 and a second point E2 respectively corresponding to mean coordinates of points that belong to both the target image 1010a and the spheres 1021 and 1022. Respective radii of the spheres 1021 and 1022 may be set such that points that belong to both the target image 1010a and the spheres 1021 and 1022 may adequately exist. For example, ⅓ of the distance between the both end points S1 and E1 may be set as the radius of each of the spheres 1021 and 1022.

The image processing unit 420 acquires a point M2 to which a distance from the first point S2 is equal to a distance from the second point E2 from among the points belonging to the target image 1010a. In other words, the distance between the first point S2 and the point M2 is equal to that between the second point E2 and the point M2. A plurality of points to each of which a distance from the first point S2 is equal to a distance from the second point E2 exist among the points belonging to the target image 1010a. The image processing unit 420 may acquire one of the plurality of points as the point M2.

The image processing unit 420 sets a sphere 1023 having the point M2 as its center. The image processing unit 420 acquires a third point M3 corresponding to a mean coordinate of points that belong to both the target image 1010a and the sphere 1023.

The image processing unit 420 may determine a section passing through the first point S2, the second point E2, and the third point M3, as the longitudinal section of the target image 1010a. The image processing unit 420 may measure the length of the target bone, based on the distance between the first point S2 and the second point E2. The image processing unit 420 may acquire a center axis of the target bone, based on the distance between the first point S2 and the second point E2.

FIG. 12 illustrates a method of determining the longitudinal section of the target image, but the longitudinal section of the target image may be determined according to various other methods.

As such, according to an embodiment of the present invention, an ultrasound diagnosis apparatus and method capable of efficiently measuring at least one selected from a location and a length of a target bone may be provided.

The image processing unit 420 may acquire a boundary surface of a soft tissue by using at least one selected from an active contour algorithm, segmentation using a cylindrical coordinate system transform, and slice-based segmentation.

Figure 13A:
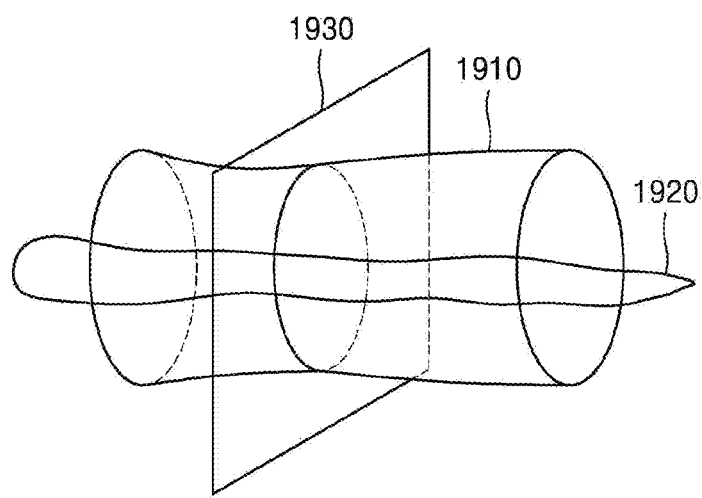
FIGS. 13A-13E explain a process in which the ultrasound diagnosis apparatus acquires a boundary surface of a soft tissue by using an active contour algorithm, according to an exemplary embodiment of the present invention.
Figure 13B:
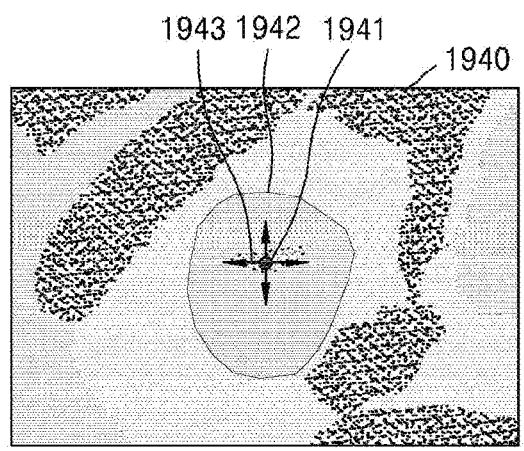
Figure 13C:
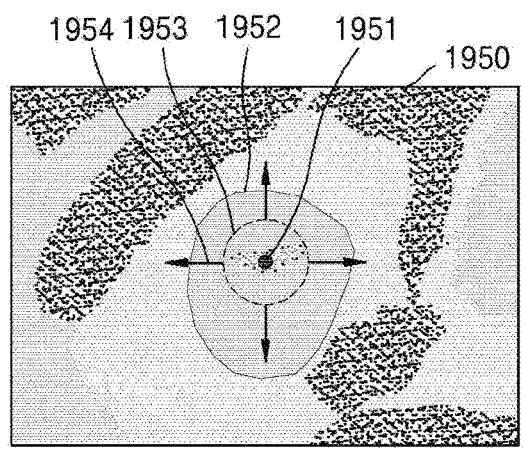
Figure 13D:
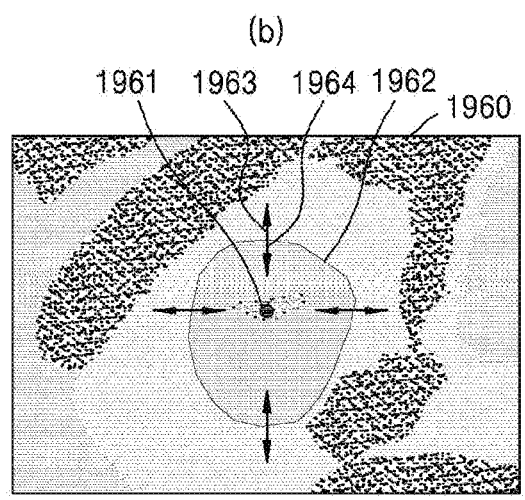
Figure 13E:
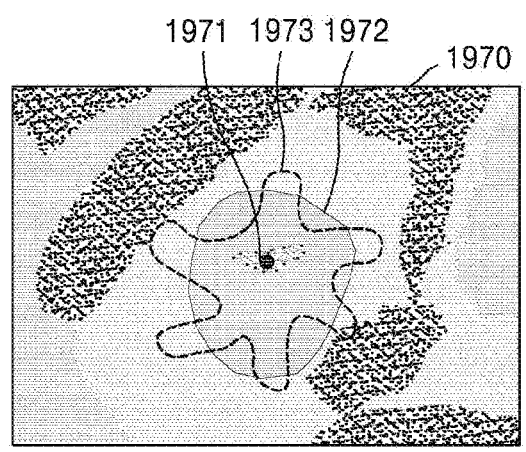

FIGS. 13A and 13E explain a process in which the ultrasound diagnosis apparatus 400 acquires a boundary surface of a soft tissue by using an active contour algorithm, according to an embodiment of the present invention.

FIG. 13A illustrates an example of a 3D ultrasound image based on volume data including a boundary surface 1910 of a soft tissue and a target bone 1920. For convenience of illustration, FIG. 13A clearly illustrates the boundary surface 1910 of the soft tissue and the target bone 1920. However, in an actual ultrasound image, a boundary between the boundary surface 1910 of the soft tissue and the target bone 1920 is not distinct due to noise or the like. This is equally applied to FIGS. 13B and 13C, and thus will not be repeatedly described. For convenience of explanation, a method of acquiring a boundary of a soft tissue from a 3D ultrasound image based on volume data will now be described. However, embodiments of the present invention are not limited thereto, and the boundary of the soft tissue may be directly acquired from the volume data.

The image processing unit 420 may acquire the first information about at least one selected from the location of the target bone within the ultrasound image and the length of the target bone, based on the volume data included in the ultrasound image data, and acquire the boundary surface of the soft tissue that is adjacent to the target bone, based on the first information. According to an embodiment of the present invention, the image processing unit 420 may automatically acquire the boundary surface of the soft tissue, based on the ultrasound image data acquired by the data acquisition unit 410. The image processing unit 420 may use pre-stored data to automatically acquire the boundary surface of the soft tissue. Since the boundary surface of the soft tissue may be acquired without special manipulations, a user may more easily use the ultrasound diagnosis apparatus 400.

According to another embodiment of the present invention, the image processing unit 420 may semi-automatically acquire the boundary surface of the soft tissue, based on at least one input received from a user. For example, the ultrasound diagnosis apparatus 400 may receive only an ancillary portion of a process of acquiring the boundary surface of the soft tissue from a user and acquire the boundary surface of the soft tissue. The ultrasound diagnosis apparatus 400 may receive an input including a predetermined ratio, a predetermined function, and a predetermined specific condition from the user. The ultrasound diagnosis apparatus 400 may receive a region of interest from the user. The ultrasound diagnosis apparatus 400 may correct information automatically acquired thereby, based on a user input.

As described above with reference to FIGS. 10-12, the ultrasound diagnosis apparatus 400 may acquire at least one selected from a location and a length of the target bone 1920 from the volume data. The boundary surface 1910 of the soft tissue may be acquired based on the acquired at least one selected from the location and the length of the target bone 1920. The ultrasound diagnosis apparatus 400 may acquire the boundary surface 1910 of the soft tissue, which covers a predetermined length of the target bone 1920. The image processing unit 420 may acquire the boundary surface of the soft tissue such that a ratio of the length of the target bone to the length of the boundary surface of the soft tissue has a predetermined ratio in a lengthwise direction of the target bone. The predetermined ratio may include at least one selected from a pre-determined ratio and a ratio received from a user.

For example, according to an embodiment of the present invention, the ultrasound diagnosis apparatus 400 may receive a predetermined ratio from a user. Alternatively, the ultrasound diagnosis apparatus 400 may previously store a predetermined ratio. For example, the predetermined ratio received from a user or the pre-stored predetermined ratio may be 50%. The ultrasound diagnosis apparatus 400 may acquire the boundary surface 1910 of the soft tissue, which covers 50% of the length of the target bone 1920 and of which a center coincides with the center point of the target bone 1920. According to another embodiment of the present invention, the predetermined ratio received from a user or the pre-stored predetermined ratio may be 150%. The ultrasound diagnosis apparatus 400 may acquire the boundary surface 1910 of the soft tissue, which covers 150% of the length of the target bone 1920 and of which a center coincides with the center point of the target bone 1920.

For example, the image processing unit 420 may extend a predetermined boundary surface from the target bone to the boundary surface of the soft tissue on the ultrasound image, by using an active contour algorithm. The image processing unit 420 may acquire an extension parameter enabling the predetermined boundary surface to extend to the boundary surface of the soft tissue on the ultrasound image, a suppression parameter having a sign reverse to that of the extension parameter and suppressing the predetermined boundary surface from exceeding the boundary surface of the soft tissue, and a smoothness parameter having an absolute value that decreases with a decrease in a change rate of an inclination of the predetermined boundary surface at a predetermined point. The image processing unit 420 may acquire the boundary surface of the soft tissue, based on a predetermined function including the extension parameter, the suppression parameter, and the smoothness parameter. A function suitable for acquiring the boundary surface of the soft tissue may be used as the predetermined function. When a value of a function that is based on parameters at the predetermined boundary surface satisfies a predetermined specific condition, the image processing unit 420 may acquire the predetermined boundary surface as the boundary surface of the soft tissue. The predetermined specific condition may vary according to a definition of a function. For example, the predetermined specific condition may include a case where values of the function are a maximum value, a minimum value, and an intermediate value.

For example, a predetermined function including an extension parameter a, a suppression parameter b, and a smoothness parameter c may be expressed as follows:

$$f(a,b,c)=|a+b+c|$$

In other words, the predetermined function may be an absolute value of a sum of the extension parameter a, the suppression parameter b, and the smoothness parameter c. The image processing unit 420 may calculate a function value at the predetermined boundary surface. The image processing unit 420 may acquire, as the boundary surface of the soft tissue, a predetermined boundary surface when a function value satisfies a specific condition. For example, the image processing unit 420 may acquire a predetermined boundary surface when a function value has a minimum value, as the boundary surface of the soft tissue.

FIG. 13B illustrates an ultrasound image 1940 of a longitudinal section 1930 of FIG. 13A. An active contour algorithm may be performed on a 3D ultrasound image. However, for convenience of explanation, in FIG. 13B, an active contour algorithm is performed on a 2D ultrasound image. In other words, the longitudinal section 1930 of FIG. 13B is for convenience of explanation, and an actual longitudinal section may not be acquired.

The ultrasound image 1940 may include a boundary 1941 of the target bone and a boundary surface 1942 of a soft tissue. Since the boundary surface 1942 of the soft tissue is still voxel data on the ultrasound image 1940, a user may visually recognize the boundary surface 1942 of the soft tissue. However, the ultrasound diagnosis apparatus 400 may not ascertain a location of the boundary surface 1942 of the soft tissue. In the related art, a user directly marks the boundary surface 1942 of the soft tissue such that the ultrasound diagnosis apparatus 400 may recognize a location of the boundary surface 1942 of the soft tissue. However, according to an embodiment of the present invention, the ultrasound diagnosis apparatus 400 may automatically acquire the location of the boundary surface 1942 of the soft tissue.

Referring to FIGS. 10-12, the ultrasound diagnosis apparatus 400 acquires a location of the boundary 1941 of the target bone. The ultrasound diagnosis apparatus 400 may extend a predetermined boundary surface, based on the location of the boundary 1941 of the target bone. The predetermined boundary surface may be extended to the boundary surface 1942 of the soft tissue on the ultrasound image by the extension parameter. A size and a direction of the extension parameter 1943 may be shown as a vector. The direction of the extension parameter may be a direction of extension from the boundary 1941 of the target bone. The size of the extension parameter may depend on a luminance change rate of a voxel at each point of the predetermined boundary surface on the ultrasound image 1940. For example, the size of the extension parameter may increase with a decrease in a luminance change rate of a voxel at each point on the predetermined boundary surface in the direction of the extension parameter.

There may exist an extension parameter 1943 and a suppression parameter (not shown) that is opposite to the extension parameter 1943. The direction of the suppression parameter may be reverse to the direction of the extension parameter 1943. The size of the suppression parameter may increase with a decrease in a luminance change rate of a voxel at each point on the predetermined boundary surface in the direction of the suppression parameter. Since a luminance change rate of a voxel between the boundary 1941 of the target bone and the boundary surface 1942 of the soft tissue on the ultrasound image 1940 is not great, the size of the extension parameter may be greater than that of the suppression parameter. A sum of the values of the extension parameter and the suppression parameter may approximate to the value of the extension parameter. Thus, the predetermined boundary surface may be gradually extended toward the boundary surface 1942 of the soft tissue on the ultrasound image 1940 by the extension parameter.

FIG. 13C illustrates an ultrasound image 1950 that is connected to FIG. 13B. FIG. 13C illustrates a case where a predetermined boundary surface 1953 is larger than a target bone 1951 and is smaller than a boundary surface 1952 of the soft tissue. Since a luminance change rate of a voxel at each point on the predetermined boundary surface 1953 is not large, an extension parameter 1954 may be greater than the suppression parameter. Thus, a sum of the extension parameter 1954 and the suppression parameter may approximate to the extension parameter 1954. Thus, the predetermined boundary surface 1953 may be further extended by the extension parameter 1954.

FIG. 13D illustrates an ultrasound image 1960 that is connected to FIG. 13C. FIG. 13D illustrates a case where a predetermined boundary surface approximates to a boundary surface 1962 of the soft tissue. When the predetermined boundary surface approximates to the boundary surface 1962 of the soft tissue, a luminance change rate of a voxel may increase. Thus, an extension parameter 1963 and a suppression parameter 1964 may equal to each other at one moment. The predetermined boundary surface may no longer extend nor reduced. In this case, the predetermined boundary surface may be acquired as the boundary surface of the soft tissue.

FIG. 13E illustrates an ultrasound image 1970 for explaining a smoothness parameter in an active contour algorithm.

The smoothness parameter has an absolute value that decreases with a decrease in a change rate of an inclination of a predetermined boundary surface 1973 at a predetermined point. The smoothness parameter may prevent the predetermined boundary surface 1973 from being greatly bent.

A sum of the extension parameter and the suppression parameter may differ at each point on the predetermined boundary surface 1973. Due to the difference between the sums of the extension parameter and the suppression parameter, points on the predetermined boundary surface 1973 may extend at different ratios. As shown in FIG. 13E, the predetermined boundary surface 1973 may not be flat. Since a change rate of an inclination of the predetermined boundary surface 1973 of FIG. 13E at each point is high, the value of the smoothness parameter may increase.

To address this problem, the smoothness parameter may be considered. In other words, the image processing unit 420 may acquire the boundary surface of the soft tissue, based on a predetermined function including an extension parameter, a suppression parameter, and a smoothness parameter. The predetermined function may be set using various methods in order to acquire an optimal boundary surface of a soft tissue. For example, the image processing unit 420 may sum an extension parameter, a suppression parameter, and a smoothness parameter on a predetermined boundary surface and calculate an absolute value of the sum. The image processing unit 420 may acquire a predetermined boundary surface when the calculated absolute value has a minimum value, as the boundary surface of the soft tissue. In this case, unevenness as in the case of the predetermined boundary surface 1973 may be prevented in consideration of the smoothness parameter.

FIGS. 14A-14D explain a process in which the ultrasound diagnosis apparatus 400 acquires a boundary surface of a soft tissue via segmentation using a cylindrical coordinate system transform, according to an embodiment of the present invention.

The image processing unit 420 may acquire the boundary surface of the soft tissue via segmentation using a cylindrical coordinate system transform. The image processing unit 420 may transform the ultrasound image to a cylindrical coordinate system and extend the predetermined boundary surface from the target bone to the boundary surface of the soft tissue on the ultrasound image. The image processing unit 420 may acquire a variation parameter of which an absolute value decreases with an increase in the luminance change rate of a voxel in the ultrasound image transformed to the cylindrical coordinate system, and a smoothness parameter of which an absolute value decreases with a decrease in the change rate of an inclination of the predetermined boundary surface decreases. The image processing unit 420 may acquire the boundary surface of the soft tissue, based on a predetermined function including the variation parameter and the smoothness parameter. The image processing unit 420 may acquire a predetermined boundary surface when an absolute value of a sum of the extension parameter, the suppression parameter, and the smoothness parameter is at a minimum, as the boundary surface of the soft tissue.

Figure 14A:
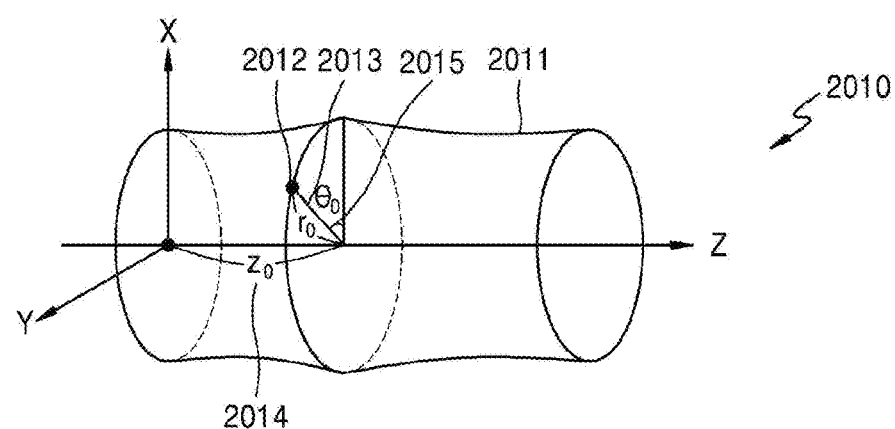
FIGS. 14A-14D explain a process in which the ultrasound diagnosis apparatus acquires a boundary surface of a soft tissue via segmentation using a cylindrical coordinate system transform, according to an exemplary embodiment of the present invention.

For convenience of illustration, FIG. 14A clearly illustrates a boundary surface 2011 of a soft tissue. However, in an actual ultrasound image, the boundary surface 2011 of the soft tissue is not distinct due to noise or the like. This is equally applied to FIG. 14B, and thus will not be further mentioned. For convenience of explanation, a method of acquiring a boundary of a soft tissue from a 3D ultrasound image 2010 based on volume data will now be described. However, embodiments of the present invention are not limited thereto, and the boundary of the soft tissue may be directly acquired from the volume data.

The ultrasound diagnosis apparatus 400 may transform the 3D ultrasound image 2010 from an orthogonal coordinate system (X, Y and Z axes) to a cylindrical coordinate system (r, θ and Z axes). For example, the 3D ultrasound image 2010, which is provided by the ultrasound diagnosis apparatus 400, may be displayed on the X, Y and Z axes. Based on the location of the target bone acquired as described above with reference to FIGS. 10-12, a central axis of the target bone may be aligned with the Z axis.

The ultrasound diagnosis apparatus 400 may acquire the boundary surface 2011 of the soft tissue, which covers a predetermined length of the target bone. For example, according to an embodiment of the present invention, the ultrasound diagnosis apparatus 400 may receive a predetermined ratio from a user. Alternatively, the ultrasound diagnosis apparatus 400 may previously store a predetermined ratio. For example, the predetermined ratio received from a user or the pre-stored predetermined ratio may be 50%. The image processing unit 420 may acquire a boundary surface 2011 of the soft tissue that covers 50% of the length of the target bone and of which a center coincides with the center point of the target bone according to the predetermined ratio. According to another embodiment of the present invention, the predetermined ratio may be 150%. The image processing unit 420 may acquire a boundary surface 2011 of the soft tissue that covers 150% of the length of the target bone and of which a center coincides with the center point of the target bone.

An arbitrary point 2012 within the 3D ultrasound image 2010 is $Z_0$ (2014) apart from an X-Y plane in a z-axis direction. The point 2012 is inclined at $\theta_0$ (2015) with respect to an X-Z plane. The point 2012 is $\theta_0$ (2013) apart from a Z axis. The point 2012 may be displayed at coordinates ($r_0, \theta_0, Z_0$) on the r, $\theta$ and Z axes. Each point in the 3D ultrasound image 2010 displayed on the X, Y and Z axes (orthogonal coordinate system) may be displayed on the r, $\theta$, and Z axes (orthogonal coordinate system).

Figure 14B:
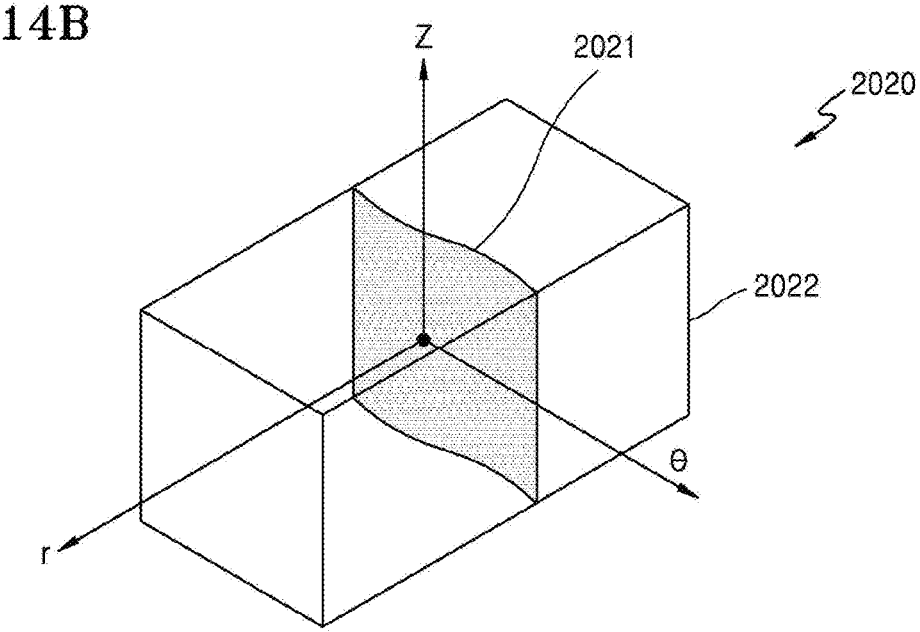

FIG. 14B illustrates a 3D ultrasound image 2020 obtained by displaying the 3D ultrasound image 2010 of FIG. 14A in a cylindrical coordinate system.

In FIG. 14B, points of the 3D ultrasound image 2020 are displayed on the r, $\theta$ and Z axes. The 3D ultrasound image 2020 may include a boundary surface 2021 of a soft tissue. Since the boundary surface 2021 of the soft tissue is still pixel data on the 3D ultrasound image 2020, a user may visually recognize the boundary surface 2021 of the soft tissue. However, the ultrasound diagnosis apparatus 400 may not ascertain a location of the boundary surface 2012 of the soft tissue. According to an embodiment of the present invention, the ultrasound diagnosis apparatus 400 may automatically acquire the location of the boundary surface 2021 of the soft tissue.

Since the central axis of the target bone coincides with the Z axis as described above with reference to FIG. 14A, an area around a $\theta$-Z plane where the coordinate value of the r axis is 0 may be a surface 2022 of the target bone in FIG. 14B. The image processing unit 420 may extend the predetermined boundary surface from the surface 2022 of the target bone to the boundary surface 2021 of the soft tissue on the 3D ultrasound image 2020. Since the boundary surface 2021 of the soft tissue has a higher r-axis value than the surface 2022 of the target bone, an r-axis coordinate value of the entire predetermined boundary surface may increase.

The image processing unit 420 may acquire a variation parameter of which an absolute value decreases with an increase in the luminance change rate of a voxel at each point of the predetermined boundary surface in the r-axis direction. For example, when the predetermined boundary surface is located near the boundary surface 2021 of the soft tissue, the luminance change rate of a voxel in the r-axis direction increases. Thus, the variation parameter may decrease near the boundary surface 2021.

The image processing unit 420 may also acquire a smoothness parameter of which an absolute value decreases with a decrease in the change rate of an inclination of the predetermined boundary surface at a predetermined point. Since the smoothness parameter has already been described above with reference to FIG. 13E, a repeated description thereof will be omitted here.

The image processing unit 420 may acquire the boundary surface 2021 of the soft tissue, based on a predetermined function including the variation parameter and the smoothness parameter. The image processing unit 420 may also acquire, as the boundary surface of the soft tissue, a predetermined boundary surface when the absolute value of a sum of the expansion parameter, the suppression parameter, and the smoothness parameter is minimum. However, it may be difficult to measure a volume of the inside of the acquired boundary surface 2021 of the soft tissue from the 3D ultrasound image 2020 displayed in the cylindrical coordinate system. Thus, the acquired boundary surface 2021 of the soft tissue may need to be transformed back to the orthogonal coordinate system.

Figure 14C:
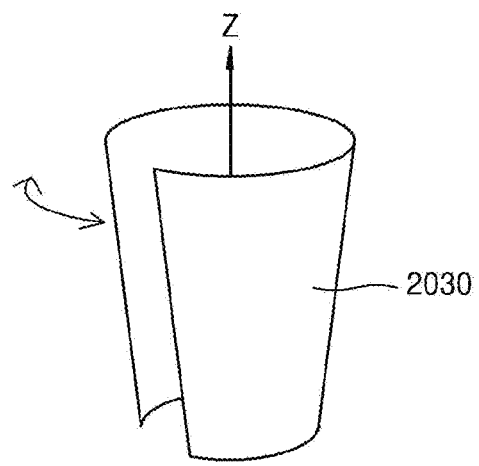

FIG. 14C illustrates a transform from a cylindrical coordinate system to an orthogonal coordinate system. In other words, coordinate transformation may be similar to an acquired boundary surface 2030 of a soft tissue surrounding the Z axis.

Figure 14D:
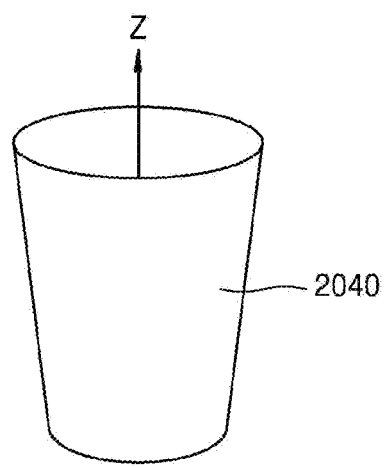

FIG. 14D illustrates a boundary surface 2040 of a soft tissue that is acquired after the transform from the cylindrical coordinate system to the orthogonal coordinate system is completed. The ultrasound diagnosis apparatus 400 may acquire a volume of the interior of the boundary surface of the soft tissue, based on the acquired boundary surface 2040 of the soft tissue.

Figure 15A:
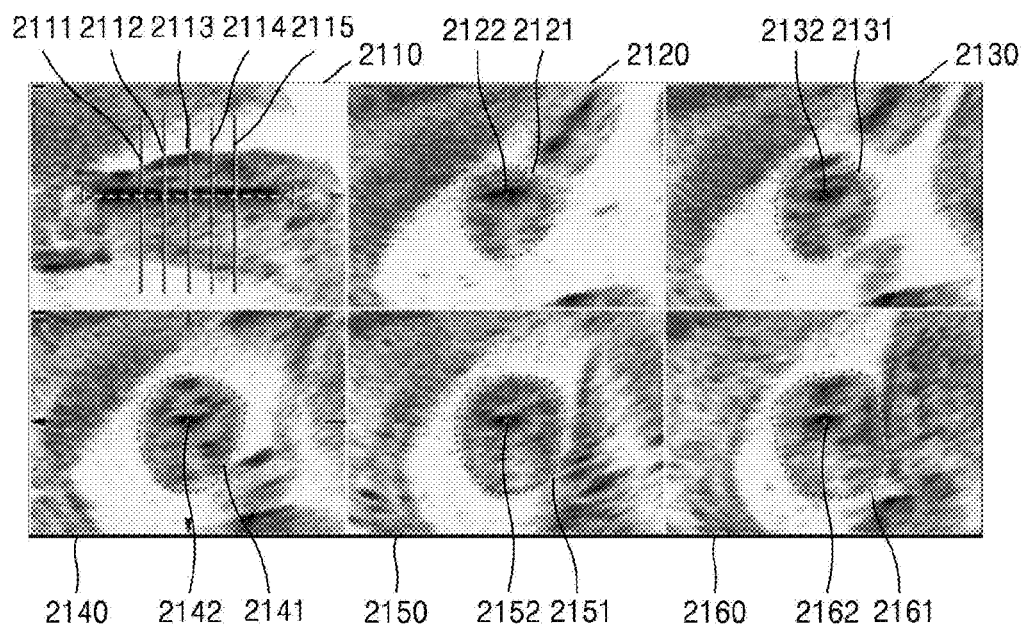
FIGS. 15A and 15B explain a method of obtaining the boundary surface of the soft tissue by using slice-based segmentation, according to an exemplary embodiment of the present invention.
Figure 15B:
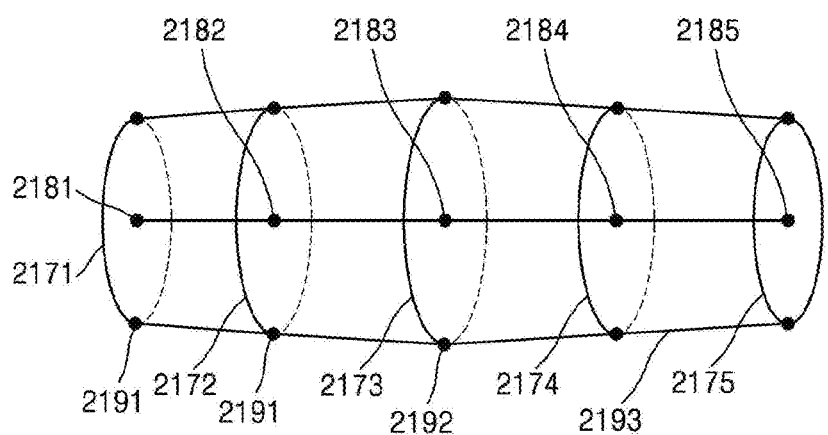

FIGS. 15A and 15B explain a method of obtaining the boundary surface of the soft tissue by using slice-based segmentation, according to an embodiment of the present invention.

The image processing unit 420 may acquire the boundary surface of the soft tissue via slice-based segmentation. The image processing unit 420 may acquire a plurality of cross-section ultrasound images that are perpendicular to the target bone. The image processing unit 420 may acquire a boundary line of the soft tissue from each of the plurality of cross-section ultrasound images. The image processing unit 420 may acquire the boundary surface of the soft tissue, based on the boundary line of the soft tissue acquired from each of the plurality of cross-section ultrasound images.

Referring to FIG. 15A, the ultrasound diagnosis apparatus 400 may acquire the boundary surface of the soft tissue, based on the location and the length of the target bone, as described above with reference to FIGS. 10-12. The ultrasound diagnosis apparatus 400 may acquire the boundary surface of the soft tissue that covers a predetermined length of the target bone. For example, according to an embodiment of the present invention, the ultrasound diagnosis apparatus 400 may acquire a boundary surface of the soft tissue that covers 50% of the length of the target bone and of which a center coincides with the center point of the target bone. According to another embodiment of the present invention, the ultrasound diagnosis apparatus 400 may acquire a boundary surface of the soft tissue that covers 150% of the length of the target bone and of which a center coincides with the center point of the target bone.

The ultrasound diagnosis apparatus 400 may acquire a plurality of longitudinal sections 2111-2115 from a 3D ultrasound image 2110. For example, the number of longitudinal sections may be 5, but embodiments of the present invention are not limited thereto. As the number of longitudinal sections increases, the accuracy of acquiring the boundary surface of the soft tissue increases. The image processing unit 420 may acquire a 2D ultrasound image 2120 of the longitudinal section 2111. The image processing unit 420 may acquire a 2D ultrasound image 2130 of the longitudinal section 2112. The image processing unit 420 may acquire a 2D ultrasound image 2140 of the longitudinal section 2113. The image processing unit 420 may acquire a 2D ultrasound image 2150 of the longitudinal section 2114. The image processing unit 420 may acquire a 2D ultrasound image 2160 of the longitudinal section 2115.

The image processing unit 420 may acquire respective boundary lines of the soft tissue from the 2D ultrasound images 2120, 2130, 2140, 2150, and 2160 according to the contour acquisition algorithm. For example, since the central axis of the target bone is acquired as described above with reference to FIGS. 10-12, a point 2122 of the central axis of the target bone may be displayed on the 2D ultrasound image 2120. The image processing unit 420 may acquire a boundary line 2121 of the soft tissue on the basis of the point 2122 of the central axis of the target bone by using a contour acquisition algorithm. A 2D active contour algorithm may be used as the contour acquisition algorithm. Likewise, boundary lines 2131, 2141, 2151, and 2161 of the soft tissue may be acquired from the ultrasound images 2130, 2140, 2150, and 2160, based on points 2132, 2142, 2152, and 2162 of the central axis of the target bone.

FIG. 15B illustrates a 3D array of the acquired boundary lines 2121, 2131, 2141, 2151 and 2161 of the soft tissue.

The boundary lines 2121, 2131, 2141, 2151 and 2161 of the soft tissue may be arranged such that the points 2122, 2132, 2142, 2152, and 2162 of the central axes of the target bone form a straight line. Intervals between the boundary lines 2121, 2131, 2141, 2151 and 2161 of the soft tissue are equal to intervals between the longitudinal sections 2111-2115 of the ultrasound image 2110 of FIG. 15A. The image processing unit 420 may acquire the boundary surface of the soft tissue, based on the boundary line of the soft tissue acquired from each of the plurality of cross-section ultrasound images.

For example, boundary lines 2171, 2172, 2173, 2174 and 2175 of the soft tissue respectively corresponding to points 2181, 2182, 2183, 2184 and 2185 of central axes of the target bone may be arranged such that the points 2181, 2182, 2183, 2184 and 2185 are aligned in a straight line. The image processing unit 420 may acquire lines that connect points on the boundary line 2172 of the soft tissue that are closest to the points on the boundary line 2171 of the soft tissue. The image processing unit 420 may also acquire a surface formed by the acquired lines, as a boundary surface of the soft tissue between the boundary lines 2171 and 2172 of the soft tissue. Likewise, the image processing unit 420 may acquire boundary surfaces of the soft tissue between the boundary lines 2172 and 2175 of the soft tissue. Since from the boundary line 2171 of the soft tissue to the boundary line 2175 of the soft tissue may be filled with an arbitrary plane, a volume of the interior of a boundary surface of the soft tissue may be acquired.

As described above with reference to FIGS. 13A-15B, a boundary surface of a soft tissue may be acquired based on ultrasound data. When the boundary surface of the soft tissue is acquired, the ultrasound diagnosis apparatus 400 may automatically acquire the volume of the interior of the boundary surface of the soft tissue.

The ultrasound diagnosis apparatus 400 may estimate the weight of an object, based on the acquired volume. The ultrasound diagnosis apparatus 400 may use statistics to estimate the weight of the object. For example, the ultrasound diagnosis apparatus 400 may have a predetermined correlation between the volume of the object and the weight thereof, based on statistics. The predetermined correlation is at least one selected from an equation, a statistical graph, and a statistical data value, and may be stored in the memory 40. The display unit 430 may display, as the predetermined correlation, at least one selected from the equation, the statistical graph, and the statistical data value.

Figure 16:
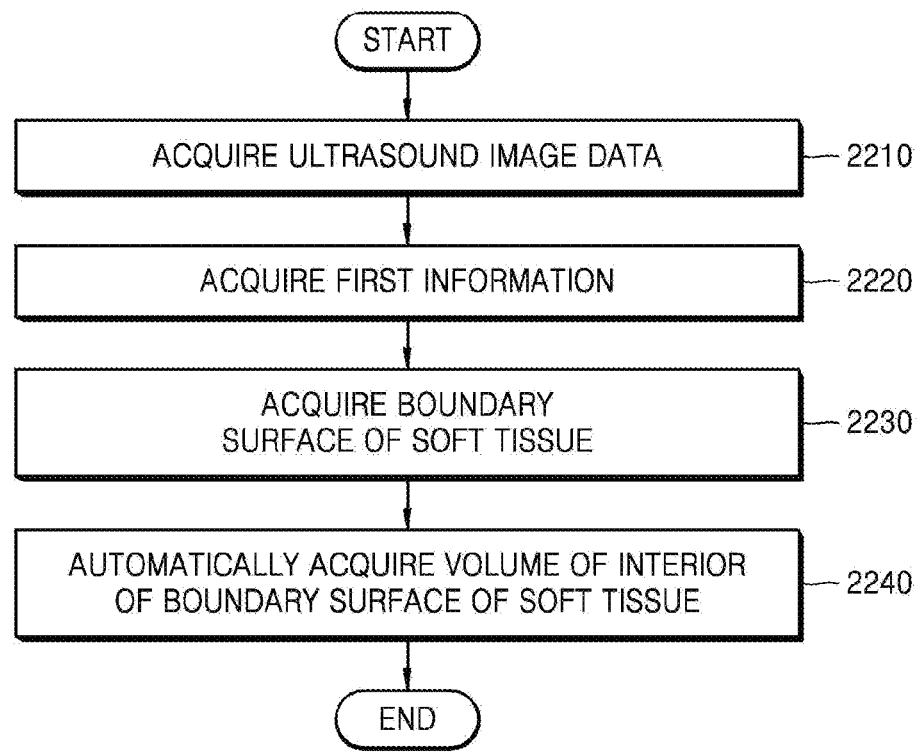
FIG. 16 is a flowchart of an ultrasound diagnosis method according to an exemplary embodiment of the present invention.

FIG. 16 is a flowchart of an ultrasound diagnosis method according to an embodiment of the present invention. Since the method of FIG. 16 is performed by the ultrasound diagnosis apparatus 400, descriptions thereof that are the same as those given above with reference to FIGS. 3-15B will be omitted here.

Referring to FIG. 16, the data acquisition unit 410 may acquire the ultrasound image data, in operation 2210. In operation 2220, the image processing unit 420 may acquire the first information. In operation 2230, the image processing unit 420 may acquire the boundary surface of the soft tissue. In operation 2240, the image processing unit 420 may automatically acquire the volume of the interior of the boundary surface of the soft tissue.

In more detail, in operation 2210, the data acquisition unit 410 may acquire the ultrasound image data regarding the object including the target bone which is to be diagnosed. In operation 2220, the image processing unit 420 may acquire the first information about at least one selected from the location of the target bone within the ultrasound image and the length of the target bone, based on the volume data included in the ultrasound image data. In operation 2230, the image processing unit 420 may acquire the boundary surface of the soft tissue that is adjacent to the target bone, based on the first information. In operation 2240, the image processing unit 420 may acquire the volume of the interior of the boundary surface of the soft tissue. The boundary surface of the soft tissue may surround at least a predetermined portion of the target bone.

The image processing unit 420 may further perform an operation of three-dimensionally rendering at least one selected from the target bone and the boundary surface of the soft tissue, based on the volume data. The display unit 430 may perform an operation of displaying an ultrasound image that is based on the ultrasound image data.

The display unit 430 may perform an operation of displaying at least one selected from: an ultrasound image that is based on a 3D-rendered target bone, a boundary surface of a 3D-rendered soft tissue, a cross section of the 3D-rendered target bone, a cross section of the boundary surface of the 3D-rendered soft tissue, and volume data; a length value of the target bone; and a volume value of the interior of the boundary surface of the soft tissue.

The display unit 430 may also perform an operation of displaying an ultrasound image on which the target bone and the soft tissue are distinguished from each other.

The display unit 430 may perform an operation of displaying at least one selected from the 3D-rendered target bone, the boundary surface of the 3D-rendered soft tissue, the cross section of the 3D-rendered target bone, and the cross section of the boundary surface of the 3D-rendered soft tissue, with different patterns, different colors, and different degrees of transparency.

The image processing unit 420 may also perform an operation of acquiring the boundary surface of the soft tissue that surrounds at least a predetermined portion of the target bone.

The operation of acquiring the boundary surface of the soft tissue may include an operation of acquiring the boundary surface of the soft tissue such that a ratio of the length of the target bone to the length of the boundary surface of the soft tissue has a predetermined ratio in a lengthwise direction of the target bone.

The predetermined ratio may include at least one selected from a pre-determined ratio and a ratio received from a user.

The image processing unit 420 may acquire a boundary surface of a soft tissue by using at least one selected from an active contour algorithm, segmentation using a cylindrical coordinate system transform, and slice-based segmentation.

In detail, according to an embodiment of the present invention, the image processing unit 420 may acquire the boundary surface of the soft tissue by using an active contour algorithm. For example, the image processing unit 420 may perform an operation of extending a predetermined boundary surface from the target bone to the boundary surface of the soft tissue on the ultrasound image. The image processing unit 420 may perform an operation of acquiring an extension parameter enabling the predetermined boundary surface to extend from the target bone to the boundary surface of the soft tissue on the ultrasound image. The image processing unit 420 may perform an operation of acquiring a suppression parameter that has an opposite sign to the extension parameter and suppresses the predetermined boundary surface from exceeding the boundary surface of the soft tissue on the ultrasound image. The image processing unit 420 may perform an operation of acquiring a smoothness parameter of which an absolute value decreases with a decrease in the change rate of an inclination of the predetermined boundary surface at a predetermined point. The image processing unit 420 may perform an operation of acquiring the boundary surface of the soft tissue, based on a predetermined function including an extension parameter, a suppression parameter, and a smoothness parameter.

According to another embodiment of the present invention, the image processing unit 420 may acquire the boundary surface of the soft tissue via segmentation using the cylindrical coordinate system transform. The image processing unit 420 may perform an operation of transforming the volume data to the cylindrical coordinate system. The image processing unit 420 may perform an operation of extending a predetermined boundary surface from the target bone to the boundary surface of the soft tissue on the ultrasound image. The image processing unit 420 may perform an operation of acquiring a variation parameter of which an absolute value decreases with an increase in a change rate of volume data transformed to the cylindrical coordinate system. The image processing unit 420 may perform an operation of acquiring a smoothness parameter of which an absolute value decreases with a decrease in the change rate of an inclination of the predetermined boundary surface. The image processing unit 420 may perform an operation of acquiring the boundary surface of the soft tissue, based on a predetermined function including a variation parameter and a smoothness parameter.

According to another embodiment of the present invention, the image processing unit 420 may acquire the boundary surface of the soft tissue via slice-based segmentation. The image processing unit 420 may perform an operation of acquiring a plurality of cross-section ultrasound images that are perpendicular to the target bone. The image processing unit 420 may perform an operation of acquiring a boundary line of the soft tissue from each of the plurality of cross-section ultrasound images. The image processing unit 420 may perform an operation of acquiring the boundary surface of the soft tissue, based on the boundary line of the soft tissue acquired from each of the plurality of cross-section ultrasound images.

According to an embodiment of the present invention, the image processing unit 420 may perform an operation of acquiring the binary ultrasound image data via thresholding based on the ultrasound image data. The image processing unit 420 may perform an operation of distinguishing a plurality of segments within the binary ultrasound image data from one another via labeling. The image processing unit 420 may perform an operation of determining one of the plurality of segments as the target image, based on image properties of the target bone. The image processing unit 420 may perform an operation of acquiring the first information based on the target image.

The operation of acquire the boundary surface of the soft tissue may include an operation of semi-automatically acquiring the boundary surface of the soft tissue, based on at least one input received from a user.

A program for executing an ultrasound diagnosis method as described above may be recorded on a computer-readable storage medium.

An ultrasound diagnosis apparatus according to an embodiment of the present invention may automatically acquire at least one selected from a location and a length of a target bone by automatically extracting ultrasound image data from a target image which is an image of the target bone. The ultrasound diagnosis apparatus may acquire a volume of a soft tissue that surrounds the target bone, based on the acquired at least one selected from the location and the length of the target bone. The embodiment of the present invention is efficient compared with the case where a user manually acquires the location and length of a target bone and the volume of a soft tissue around the target bone while viewing an image. In the case of manual measurement, a measurement deviation occurs according to the skill of a user and a subjective determination of the user. Moreover, manual measurement may require long time. According to an embodiment of the present invention, the location and length of a target bone and the volume of a soft tissue around the target bone are automatically measured, and thus the accuracy of measurement may increase. Moreover, automatic measurement may require short time.

The ultrasound diagnosis apparatus may automatically extract the target image from the volume data and automatically determine a longitudinal section from the target image. If a user has to manually acquire a longitudinal section of the target bone, accuracy may not be guaranteed due to a deviation between users. If a user has to repeat a scan to acquire the longitudinal section, a repetitive stress injury (RSI) of the user may increase. Thus, according to an embodiment of the present invention, the accuracy of measurement may increase. In addition, the RSI of the user may decrease.

The above-described methods can be written as computer programs and can be implemented in general-use digital computers that execute the programs using a non-transitory computer readable recording medium. A structure of the data used in the above-described methods may be recorded in a non-transitory computer readable recording medium via several means. Examples of the non-transitory computer readable recording medium include magnetic storage media (e.g., ROM, RAM, USB, floppy disks, hard disks, etc.), optical recording media (e.g., CD-ROMs, or DVDs), etc.

The exemplary embodiments should be considered in a descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound diagnosis apparatus comprising:
   a memory; and
   a digital computer executing a program stored in the memory, wherein execution of the program by the digital computer causes the digital computer to:
   acquire ultrasound image data regarding an object including at least one target bone which is to be diagnosed, receive a location of a target bone, among the at least one target bone, within an ultrasound image from a user,
acquire a length of the target bone, based on the location of the target bone,
determine a center point of the target bone;
acquire at least two cross-section ultrasound images comprising a first cross-section ultrasound image and a second cross-section ultrasound image from a space including at least part of the target bone, wherein longitudinal location of the first cross-section ultrasound image is determined based on a distance calculated using the length of the target bone and a first predetermined ratio, and a first direction from the center point to a first terminal of the target bone,
and longitudinal location of the second cross-section ultrasound image is determined based on a distance calculated using the length of the target bone and a second predetermined ratio, and a second direction, different from the first direction, from the center point to a second terminal of the target bone, and
acquire at least two outer boundary lines of a soft tissue, wherein the soft tissue is adjacent to the target bone, for the at least two cross-section ultrasound images,
acquire an outer boundary surface of the soft tissue that is adjacent to the target bone, based on the at least two outer boundary lines,
automatically acquire a volume of an interior of the outer boundary surface of the soft tissue including the at least two cross-section ultrasound images,
estimate, based on a correlation of a weight variable with a volume variable, a weight of the object based on the volume, and
display a value of the weight in a form of at least one selected from text, figure, color and graph.

2. The ultrasound diagnosis apparatus of claim 1, wherein the digital computer three-dimensionally renders at least one selected from the target bone and the outer boundary surface of the soft tissue, based on the volume data.

3. The ultrasound diagnosis apparatus of claim 2, further comprising a display unit configured to display the ultrasound image that is generated by the digital computer.

4. The ultrasound diagnosis apparatus of claim 3, wherein the display unit displays at least one selected from the ultrasound image that is based on a 3D-rendered target bone, an outer boundary surface of a 3D-rendered soft tissue, a cross section of the 3D-rendered target bone, a cross section of the outer boundary surface of the 3D-rendered soft tissue, and volume data; and a length value of the target bone.

5. The ultrasound diagnosis apparatus of claim 3, wherein the display unit displays an ultrasound image on which the target bone and the soft tissue are distinguished from each other.

6. The ultrasound diagnosis apparatus of claim 5, wherein the display unit displays at least one selected from a 3D-rendered target bone, an outer boundary surface of the 3D-rendered soft tissue, a cross section of the 3D-rendered target bone, and a cross section of the outer boundary surface of the 3D-rendered soft tissue, with different patterns, different colors, and different degrees of transparency.

7. The ultrasound diagnosis apparatus of claim 1, wherein the digital computer acquires the outer boundary surface of the soft tissue by further using at least one selected from an active contour algorithm, segmentation using a cylindrical coordinate system transform, and slice-based segmentation.

8. The ultrasound diagnosis apparatus of claim 7, wherein by using the active contour algorithm, the digital computer
extends a predetermined boundary surface from the target bone to the outer boundary surface of the soft tissue on the ultrasound image,
acquires an extension parameter enabling the predetermined boundary surface to extend to the outer boundary surface of the soft tissue on the ultrasound image, a suppression parameter having an opposite sign to the extension parameter and preventing the predetermined boundary surface from exceeding the outer boundary surface of the soft tissue on the ultrasound image, and a smoothness parameter of which an absolute value decreases with a decrease in a change rate of an inclination of the predetermined boundary surface at a predetermined point, and
acquires the outer boundary surface of the soft tissue, based on a predetermined function including the extension parameter, the suppression parameter, and the smoothness parameter.

9. The ultrasound diagnosis apparatus of claim 7, wherein via the segmentation using the cylindrical coordinate system transform, the digital computer
transforms the ultrasound image to a cylindrical coordinate system,
extends a predetermined boundary surface from the target bone to the outer boundary surface of the soft tissue on the ultrasound image,
acquires a variation parameter of which an absolute value decreases with an increase in a luminance change rate of a voxel in an ultrasound image obtained by the transformation to the cylindrical coordinate system, and a smoothness parameter of which an absolute value decreases with a decrease in a change rate of an inclination of the predetermined boundary surface, and
acquires the outer boundary surface of the soft tissue, based on a predetermined function including the variation parameter and the smoothness parameter.

10. The ultrasound diagnosis apparatus of claim 1, wherein the digital computer semi-automatically acquires the boundary surface of the soft tissue, based on at least one input received from a user.

11. An ultrasound diagnosis method comprising:
acquiring ultrasound image data regarding an object including at least one target bone which is to be diagnosed;
receiving a location of a target bone, among the at least one target bone, within an ultrasound image from a user;
acquiring a length of the target bone, based on the location of the target bone;
determining a center point of the target bone;
acquiring at least two cross-section ultrasound images comprising a first cross-section ultrasound image and a second cross-section ultrasound image from a space including at least part of the target bone wherein longitudinal location of the first cross-section ultrasound image is determined based on a distance calculated using the length of the target bone and a first predetermined ratio, and a first direction from the center point to a first terminal of the target bone, and longitudinal location of the second cross-section ultrasound image is determined based on a distance calculated using the length of the target hone and a second predetermined ratio, and a second direction, different from the first direction, from the center point to a second terminal of the target bone, and acquiring at least two outer boundary lines of a soft tissue, wherein the soft tissue is adjacent to the target bone, for the at least two cross-section ultrasound images, acquiring an outer boundary surface of the soft tissue that is adjacent to the target bone, based on the at least two outer boundary lines;

automatically acquiring a volume of an interior of the outer boundary surface of the soft tissue including the at least two cross-section ultrasound images;

estimating, based on a correlation of a weight variable with a volume variable, a weight of the object based on the volume; and displaying a value of the weight in a form of at least one selected from text, figure, color and graph.

12. The ultrasound diagnosis method of claim 11, further comprising three-dimensionally rendering at least one selected from the target bone and the outer boundary surface of the soft tissue, based on the volume data.

13. The ultrasound diagnosis method of claim 12, further comprising displaying the ultrasound image that is based on the ultrasound image data.

14. The ultrasound diagnosis method of claim 13, wherein the displaying comprises displaying at least one selected from: the ultrasound image that is based on a 3D-rendered target bone, an outer boundary surface of a 3D-rendered soft tissue, a cross section of the 3D-rendered target bone, a cross section of the outer boundary surface of the 3D-rendered soft tissue, and volume data; and a length value of the target bone.

15. The ultrasound diagnosis method of claim 13, wherein the displaying comprises displaying an ultrasound image on which the target bone and the soft tissue are distinguished from each other.

16. The ultrasound diagnosis method of claim 15, wherein the displaying comprises displaying at least one selected from a 3D-rendered target bone, an outer boundary surface of the 3D-rendered soft tissue, a cross section of the 3D-rendered target bone, and a cross section of the outer boundary surface of the 3D-rendered soft tissue, with different patterns, different colors, and different degrees of transparency.

17. The ultrasound diagnosis method of claim 11, wherein the acquiring of the outer boundary surface of the soft tissue further uses at least one selected from an active contour algorithm, segmentation using a cylindrical coordinate system transform, and slice-based segmentation.

18. The ultrasound diagnosis method of claim 17, wherein the acquiring of the outer boundary surface of the soft tissue comprises, via the active contour algorithm:

extending a predetermined boundary surface from the target bone to the outer boundary surface of the soft tissue on the ultrasound image;

acquiring an extension parameter enabling the predetermined boundary surface to extend to the outer boundary surface of the soft tissue on the ultrasound image;

acquiring a suppression parameter having an opposite sign to the extension parameter and preventing the predetermined boundary surface from exceeding the outer boundary surface of the soft tissue on the ultrasound image;

acquiring a smoothness parameter of which an absolute value decreases with a decrease in a change rate of an inclination of the predetermined boundary surface at a predetermined point; and acquiring the outer boundary surface of the soft tissue, based on a predetermined function including the extension parameter, the suppression parameter, and the smoothness parameter.

19. The ultrasound diagnosis method of claim 17, wherein the acquiring of the outer boundary surface of the soft tissue comprises, via the segmentation using the cylindrical coordinate system transform:

transforming the ultrasound image to a cylindrical coordinate system;

extending a predetermined boundary surface from the target bone to the outer boundary surface of the soft tissue on the ultrasound image;

acquiring a variation parameter of which an absolute value decreases with an increase in a luminance change rate of a voxel in an ultrasound image obtained by the transformation to the cylindrical coordinate system;

acquiring a smoothness parameter of which an absolute value decreases with a decrease in a change rate of an inclination of the predetermined boundary surface; and acquiring the outer boundary surface of the soft tissue, based on a predetermined function including the variation parameter and the smoothness parameter.

20. The ultrasound diagnosis method of claim 11, wherein the acquiring of the outer boundary surface of the soft tissue comprises semi-automatically acquiring the outer boundary surface of the soft tissue, based on at least one input received from a user.

21. A non-transitory computer-readable recording medium having recorded thereon a program for causing a computer to execute a process for ultrasound diagnosis, the process comprising:

acquiring ultrasound image data regarding an object including at least one target bone which is to be diagnosed;

acquiring a length of the target bone, based on the location of the target bone;

determining a center point of the target bone;

acquiring at least two cross-section ultrasound images comprising a first cross-section ultrasound image and a second cross-section ultrasound image from a space including at least part of the target bone, wherein longitudinal location of the first cross-section ultrasound image is determined based on a distance calculated using the length of the target bone and a first predetermined ratio, and a first direction from the center point to a first terminal of the target bone, and longitudinal location of the second cross-section ultrasound image is determined based on a distance calculated using the length of the target bone and a second predetermined ratio, and a second direction, different from the first direction, from the center point to a second terminal of the target bone, and acquiring at least two outer boundary lines of a soft tissue, wherein the soft tissue is adjacent to the target bone, for the at least two cross-section ultrasound images, acquiring an outer boundary surface of the soft tissue that is adjacent to the target bone, based on the at least two outer boundary lines;

automatically acquiring a volume of an interior of the outer boundary surface of the soft tissue including the at least two cross-section ultrasound images;

estimating, based on a correlation of a weight variable with a volume variable, a weight of the object based on the volume; and displaying a value of the weight in a form of at least one selected from text, figure, color and graph.

22. The ultrasound diagnosis apparatus of claim 1, wherein the digital computer acquires an outer boundary surface of the soft tissue that surrounds at least a predetermined portion of the target bone.

23. The ultrasound diagnosis apparatus of claim 22, wherein the digital computer acquires the outer boundary surface of the soft tissue such that a ratio of the length of the target bone to a length of the outer boundary surface of the soft tissue has a predetermined ratio, in a lengthwise direction of the target bone.

24. The ultrasound diagnosis apparatus of claim 23, wherein the predetermined ratio comprises at least one selected from a pre-determined ratio and a ratio received from a user.

25. The ultrasound diagnosis method of claim 11, wherein the acquiring an outer boundary surface of the soft tissue comprises acquiring an outer boundary surface of the soft tissue that surrounds at least a predetermined portion of the target bone.

26. The ultrasound diagnosis method of claim 25, wherein the acquiring of the outer boundary surface of the soft tissue comprises acquiring the outer boundary surface of the soft tissue such that a ratio of the length of the target bone to a length of the outer boundary surface of the soft tissue has a predetermined ratio, in a lengthwise direction of the target bone.

27. The ultrasound diagnosis method of claim 26, wherein the predetermined ratio comprises at least one selected from a pre-determined ratio and a ratio received from a user.

\* \* \* \* \*